US011267808B2

(12) United States Patent
Castro Palomino Laria et al.

(10) Patent No.: US 11,267,808 B2
(45) Date of Patent: Mar. 8, 2022

(54) BENZAMIDE DERIVATIVES AS PPAR-GAMMA MODULATORS

(71) Applicant: MEDIBIOFARMA, S.L., Navarra (ES)

(72) Inventors: Julio Castro Palomino Laria, Barcelona (ES); Juan Camacho Gómez, Barcelona (ES); Rodolfo Rodríguez Iglesias, Barcelona (ES)

(73) Assignee: Medibiofarma, S.L., Navarra (ES)

( * ) Notice: Subject to any disclaimer, the term of this patent is extended or adjusted under 35 U.S.C. 154(b) by 0 days.

(21) Appl. No.: 16/771,514

(22) PCT Filed: Dec. 11, 2018

(86) PCT No.: PCT/EP2018/084290
§ 371 (c)(1),
(2) Date: Jun. 10, 2020

(87) PCT Pub. No.: WO2019/115498
PCT Pub. Date: Jun. 20, 2019

(65) Prior Publication Data
US 2021/0171511 A1 Jun. 10, 2021

(30) Foreign Application Priority Data

Dec. 12, 2017 (EP) .................................... 17382845

(51) Int. Cl.
*A61K 45/06* (2006.01)
*C07D 413/04* (2006.01)
*C07D 213/75* (2006.01)
*C07D 237/20* (2006.01)
*C07D 401/04* (2006.01)

(52) U.S. Cl.
CPC ............ *C07D 413/04* (2013.01); *A61K 45/06* (2013.01); *C07D 213/75* (2013.01); *C07D 237/20* (2013.01); *C07D 401/04* (2013.01)

(58) Field of Classification Search
None
See application file for complete search history.

(56) References Cited

U.S. PATENT DOCUMENTS

2003/0134859 A1  7/2003  Amemiya et al.
2008/0206194 A1  8/2008  Glazer

FOREIGN PATENT DOCUMENTS

EP    1277729 A1    1/2003
JP    2003073357 A  3/2003

OTHER PUBLICATIONS

Chawla, Ajay, et al. Nuclear receptors and lipid physiology: opening the X-files. Science, 2001, vol. 294, No. 5548, p. 1866-1870.

Chawla, Ajay, et al. Peroxisome proliferator-activated receptor (PPAR) gamma: adipose-predominant expression and induction early in adipocyte differentiation. Endocrinology, 1994, vol. 135, No. 2, p. 798-800.

Berger, Joel; Moller, David E. The mechanisms of action of PPARs. Annual review of medicine, 2002, vol. 53, No. 1, p. 409-435.

Burton, Jack D.; Goldenberg, David M.; Blumenthal, Rosalyn D. Potential of peroxisome proliferator-activated receptor gamma antagonist compounds as therapeutic agents for a wide range of cancer types. PPAR research, 2008, vol. 2008.

Panigrahy, Dipak, et al. Therapeutic potential of thiazolidinediones as anticancer agents. Expert opinion on investigational drugs, 2003, vol. 12, No. 12, p. 1925-1937.

Yousefi, Bahman, et al. Peroxisome Proliferator-Activated Receptor Ligands and Their Role in Chronic Myeloid Leukemia: Therapeutic Strategies. Chemical biology & drug design, 2016, vol. 88, No. 1, p. 17-25.

Elstner, Elena, et al. Ligands for peroxisome proliferator-activated receptor γ and retinoic acid receptor inhibit growth and induce apoptosis of human breast cancer cells in vitro and in BNX mice. Proceedings of the National Academy of Sciences, 1998, vol. 95, No. 15, p. 8806-8811.

Chang, Tsg-Hui; Szabo, Eva. Induction of differentiation and apoptosis by ligands of peroxisome proliferator-activated receptor γ in non-small cell lung cancer. Cancer research, 2000, vol. 60, No. 4, p. 1129-1138.

(Continued)

*Primary Examiner* — Samantha L Shterengarts
(74) *Attorney, Agent, or Firm* — Gary J. Gershik; Amster Rothstein & Ebenstein LLP

(57) ABSTRACT

The present invention relates to novel benzamides derivatives of formula (I)

(I)

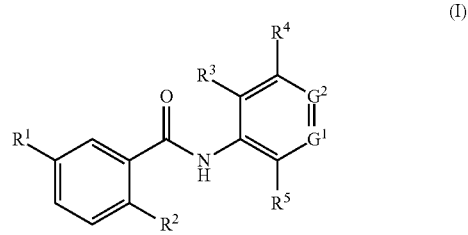

as modulators of PPAR-gamma receptor, to processes for their preparation, to pharmaceutical compositions comprising said compounds and to said compound for use in the treatment of pathological conditions, disorders or diseases that can improve by modulation of PPAR-gamma receptor, such as cancer; metabolic diseases, inflammatory diseases, respiratory disorders, autoimmune diseases, neurodegenerative diseases, cardiovascular diseases and renal diseases.

18 Claims, No Drawings

(56) References Cited

OTHER PUBLICATIONS

Reddy, Aravind T.; Lakshmi, Sowmya P.; Reddy, Raju C. PPAR-gamma as a novel therapeutic target in lung cancer. PPAR research, 2016, vol. 2016.

Takenokuchi, M., et al. Troglitazone inhibits cell growth and induces apoptosis of B-cell acute lymphoblastic leukemia cells with t (14; 18). Acta Haematologica, 2006, vol. 116, No. 1, p. 30-40.

Mueller, Elisabetta, et al. Terminal differentiation of human breast cancer through PPAR-gamma. Molecular cell, 1998, vol. 1, No. 3, p. 465-470.

Goldstein, Jonathan T., et al. Genomic activation of PPARG reveals a candidate therapeutic axis in bladder cancer. Cancer Research, 2017, p. canres. 1701.2017.

Masuda, Tomotake, et al. Critical role of peroxisome proliferator-activated receptor γ on anoikis and invasion of squamous cell carcinoma. Clinical Cancer Research, 2005, vol. 11, No. 11, p. 4012-4021.

Burton, Jack D., et al. Peroxisome proliferator-activated receptor-γ antagonists exhibit potent antiproliferative effects versus many hematopoietic and epithelial cancer cell lines. Anti-cancer drugs, 2007, vol. 18, No. 5, p. 525-534.

Garcia-Bates, Tatiana M., et al. Peroxisome proliferator-activated receptor gamma overexpression and knockdown: impact on human B cell lymphoma proliferation and survival. Cancer immunology, immunotherapy, 2009, vol. 58, No. 7, p. 1071-1083.

Im, Chang-Nim. Combination Treatment with PPARγ Ligand and Its Specific Inhibitor GW9662 Downregulates BIS and 14-3-3 Gamma, Inhibiting Stem-Like Properties in Glioblastoma Cells. BioMed Research International, 2017, vol. 2017.

Berger, Joel P.; Akiyama, Taro E.; Meinke, Peter T. PPARs: therapeutic targets for metabolic disease. Trends in pharmacological sciences, 2005, vol. 26, No. 5, p. 244-251.

Han, Lu, et al. PPARs: regulators of metabolism and as therapeutic targets in cardiovascular disease. Part II: PPAR-62 /δ and PPAR-γ. Future cardiology, 2017.

Li, Andrew C., et al. Peroxisome proliferator-activated receptor γ ligands inhibit development of atherosclerosis in LDL receptor-deficient mice. The Journal of clinical investigation, 2000, vol. 106, No. 4, p. 523-531.

Hsueh, Willa A.; Bruemmer, Dennis. Peroxisome proliferator-activated receptor γ: implications for cardiovascular disease. Hypertension, 2004, vol. 43, No. 2, p. 297-305.

Neuschwander-Tetri, Brent A., et al. Improved nonalcoholic steatohepatitis after 48 weeks of treatment with the PPAR-γ ligand rosiglitazone. Hepatology, 2003, vol. 38, No. 4, p. 1008-1017.

Krishnan, Jaya, et al. Activation of a HIF1α-PPARγ axis underlies the integration of glycolytic and lipid anabolic pathways in pathologic cardiac hypertrophy. Cell metabolism, 2009, vol. 9, No. 6, p. 512-524.

Kintscher, Ulrich; Law, Ronald E. PPARγ-mediated insulin sensitization: the importance of fat versus muscle. American Journal of Physiology-Endocrinology and Metabolism, 2005, vol. 288, No. 2, p. E287-E291.

Park, Kyong Soo, et al. PPAR-γ gene expression is elevated in skeletal muscle of obese and type II diabetic subjects. Diabetes, 1997, vol. 46, No. 7, p. 1230-1234.

Daynes, Raymond A.; Jones, Dallas C. Emerging roles of PPARs in inflammation and immunity. Nature reviews. Immunology, 2002, vol. 2, No. 10, p. 748.

Kostadinova, Radina; Wahli, Walter; Michalik, Liliane. PPARs in diseases: control mechanisms of inflammation. Current medicinal chemistry, 2005, vol. 12, No. 25, p. 2995-3009.

Ricote, Mercedes; Glass, Christopher K. PPARs and molecular mechanisms of transrepression. Biochimica et Biophysica Acta (BBA)-Molecular and Cell Biology of Lipids, 2007, vol. 1771, No. 8, p. 926-935.

Ryan, Michael J., et al. PPARα agonist rosiglitazone improves vascular function and lowers blood pressure in hypertensive transgenic mice. Hypertension, 2004, vol. 43, No. 3, p. 661-666.

Sundararajan, Sophia, et al. PPARγ as a therapeutic target in central nervous system diseases. Neurochemistry international, 2006, vol. 49, No. 2, p. 136-144.

Abushouk, Abdelrahman Ibrahim, et al. Peroxisome proliferator-activated receptors as therapeutic targets for heart failure. Biomedicine & Pharmacotherapy, 2017, vol. 95, p. 692-700.

Sato, Kazuya, et al. PPARγ antagonist attenuates mouse immune-mediated bone marrow failure by inhibition of T cell function. Haematologica, 2016, vol. 101, No. 1, p. 57-67.

Park, Hong-Jai, et al. PPARγ negatively regulates T cell activation to prevent follicular helper T cells and germinal center formation. PloS one, 2014, vol. 9, No. 6, p. e99127.

Rieusset, Jennifer, et al. A new selective peroxisome proliferator-activated receptor γ antagonist with antiobesity anti antidiabetic activity. Molecular Endocrinology, 2002, vol. 16, No. 11, p. 2628-2644.

Doggrell, Sheila. Do peroxisome proliferation receptor-γ antagonists have clinical potential as combined antiobesity and antidiabetic drugs?. Expert opinion on investigational drugs, 2003, vol. 12, No. 4, p. 713-716.

Duque, Gustavo, et al. Pharmacological inhibition of PPARγ increases osteoblastogenesis and bone mass in male C57BL/6 mice. Journal of Bone and Mineral Research, 2013, vol. 28, No. 3, p. 639-648.

Ferry, Gilles, et al. Binding of prostaglandins to human PPARγ: tool assessment and new natural ligands. European journal of pharmacology, 2001, vol. 417, No. 1, p. 77-89.

Hara, H. and Van Der Plas, H. C. (1982), On the amination of azaheterocycles. A new procedure for the introduction of an amino group Journal of Heterocyclic Chemistry, 19: 1285-1287. doi:10.1002/jhet.5570190605.

Jiao et al., Eur. J. Med. Chem., 2015, 90, 170-183.

Nov. 9, 2021 Examination Report under Sections 12 & 13 of the Patents Act, 1970 and the Patents Rules, 2003 issued in connection with Indian Patent Application No. 202017028719.

BENZAMIDE DERIVATIVES AS PPAR-GAMMA MODULATORS

RELATED APPLICATIONS

This application is a § 371 national stage of PCT International Application No. PCT/EP2018/084290, filed Dec. 11, 2018, and claiming priority of EPO Application No. EP17382845.0, filed Dec. 12, 2017, the contents of each of which are hereby incorporated by reference into this application.

FIELD OF THE INVENTION

The present invention relates to novel, optionally substituted, benzamide derivatives as modulators of PPAR-gamma receptor.

Other objectives of the present invention are to provide a procedure for preparing these compounds; pharmaceutical compositions comprising an effective amount of these compounds; the use of the compounds for manufacturing a medicament for the treatment or prevention of pathological conditions or diseases that can improve by modulation of PPAR-gamma receptor, such as cancer disease, metabolic disorders, glucose metabolism disorder, inflammatory diseases, autoimmune disease, neurodegenerative disease, cardiovascular diseases, neoplastic diseases and renal diseases, to said compounds for use in the treatment or prevention of said diseases and to methods of treatment or prevention of said diseases.

STATE OF THE ART

Peroxisome proliferator-activated receptors (PPARs) are transcriptional factors belonging to the nuclear receptor superfamily (CHAWLA, Ajay, et al. *Nuclear receptors and lipid physiology: opening the X-files*. Science, 2001, vol. 294, no 5548, p. 1866-1870). It is predominantly expressed in adipose tissue and in a variety of cells of the immune system including monocytes, macrophages, B and T lymphocytes, natural killer cells, dendritic cells, neutrophils, eosinophils, and mast cells (CHAWLA, Ajay, et al. *Peroxisome proliferator-activated receptor (PPAR) gamma: adipose-predominant expression and induction early in adipocyte differentiation*. Endocrinology, 1994, vol. 135, no 2, p. 798-800).

PPARs are activated by small molecule ligands including endogenous saturated and unsaturated fatty acids, their metabolites and synthetic ligands. PPARs function as obligate heterodimers with retinoid X receptors (RXRs), which bind to peroxisome proliferator response elements (PPREs) that are located in the regulatory domains of genes, regulating transcription of target genes in a ligand-dependent manner. Ligand binding to PPARs stabilizes their conformation and subsequently modulates cofactor recruitment, resulting in transcriptional activation. Three subtypes with different distributions and specific roles have been identified for PPARs to date, PPARα (PPAR alpha), PPAR β/δ (PPAR beta/delta), and PPARγ (PPAR-gamma). The three PPARs differ in their structure, function, and tissue distribution (BERGER, Joel; MOLLER, David E. *The mechanisms of action of PPARs*. Annual review of medicine, 2002, vol. 53, no 1, p. 409-435).

The cardinal biologic activity of PPAR-gamma is the induction of differentiation of adipocytes, the cell type that expresses the highest levels of PPAR-gamma amongst normal tissues. Lower levels of PPAR-gamma are, however, found in other normal tissues and cell types such as skeletal muscle, liver, breast, prostate, colon, type 2 alveolar pneumocytes, some endothelial cells as well as monocytes, and B-lymphocytes. (BURTON, Jack D.; GOLDENBERG, David M.; BLUMENTHAL, Rosalyn D. *Potential of peroxisome proliferator-activated receptor gamma antagonist compounds as therapeutic agents for a wide range of cancer types*. PPAR research, 2008, vol. 2008).

PPAR-Gamma and Cancer

PPAR-gamma has become a putative therapeutic cancer target in a variety of epithelial cell tumors. It is known that PPAR-gamma activation may inhibit neoplastic processes by suppressing tumor cell replication and decreasing tumor cell survival (PANIGRAHY, Dipak, et al. *Therapeutic potential of thiazolidinediones as anticancer agents*. Expert opinion on investigational drugs, 2003, vol. 12, no 12, p. 1925-1937.).

PPAR-gamma ligands have been shown to promote differentiation and apoptosis in a variety of cancer cells including colon cancer, breast cancer, prostate cancer, gastric cancer, bladder cancer, and pancreatic cancer (YOUSEFI, Bahman, et al. *Peroxisome Proliferator-Activated Receptor Ligands and Their Role in Chronic Myeloid Leukemia: Therapeutic Strategies*. Chemical biology & drug design, 2016, vol. 88, no 1, p. 17-25, and its references). (ELSTNER, Elena, et al. *Ligands for peroxisome proliferator-activated receptor γ and retinoic acid receptor inhibit growth and induce apoptosis of human breast cancer cells in vitro and in BNX mice*. Proceedings of the National Academy of Sciences, 1998, vol. 95, no 15, p. 8806-8811). In addition, it is known that PPAR ligands show synergistic effects when is used in combination with tyrosine kinase inhibitor, such as imatinib, used in patients with chronic myeloid leukemia (CML).

Several studies have demonstrated the potential and effectiveness of PPAR-gamma agonists as novel monotherapy for lung cancer (CHANG, Tsg-Hui; SZABO, Eva. *Induction of differentiation and apoptosis by ligands of peroxisome proliferator-activated receptor γ in non-small cell lung cancer*. Cancer research, 2000, vol. 60, no 4, p. 1129-1138), and also in combination with standard cytotoxic chemotherapy. PPAR-gamma agonists demonstrate a synergistic effect with traditional chemotherapeutic agents, enhancing their cytotoxic effect on cancer cells. (REDDY, Aravind T.; LAKSHMI, Sowmya P.; REDDY, Raju C. *PPAR-gamma as a novel therapeutic target in lung cancer*. PPAR research, 2016, vol. 2016).

Likewise, peroxisome proliferator-activated receptor-gamma (PPAR-gamma) has been detected in several human leukemia cells. Recent studies reported that PPAR-gamma ligands inhibit cell proliferation and induce apoptosis in both normal and malignant B-lineage cells. (TAKENOKUCHI, M., et al. *Troglitazone inhibits cell growth and induces apoptosis of B-cell acute lymphoblastic leukemia cells with t (14; 18)*. Acta Haematologica, 2006, vol. 116, no 1, p. 30-40).

However, while PPAR-gamma activation is associated with tumor cell death in some cases, several observations suggest that the inhibition of PPAR-gamma function may also be beneficial in treating certain cancers.

PPAR-gamma is over-expressed in many epithelial tumor cells, including those of the stomach, breast and lung, and may represent a tumor survival factor (MUELLER, Elisabetta, et al. *Terminal differentiation of human breast cancer through PPAR-gamma*. Molecular cell, 1998, vol. 1, no 3, p. 465-470.)

Other studies shown that activating alterations of PPAR-gamma or RXRA lead to a specific gene expression signature in bladder cancers. Reducing PPAR-gamma activity, whether by pharmacologic inhibition or genetic ablation, inhibited proliferation of PPAR-gamma-activated bladder cancer cells. (GOLDSTEIN, Jonathan T., et al. *Genomic activation of PPARG reveals a candidate therapeutic axis in bladder cancer*. Cancer Research, 2017, p. canres. 1701.2017).

In another study the effects of the PPAR-gamma antagonists, BADGE, GW9662 and T0070907, on four squamous carcinoma cell lines derived from tumors of the oral cavity were evaluated. Antiproliferative effects were shown for the three antagonists, but not for the agonist pioglitazone, denoting that PPAR-gamma antagonist compounds with varying chemical structures have several significant anticancer effects in vitro and in vivo in epithelial cancer model systems including breast, colon, aerodigestive squamous cell, and hepatocellular. (MASUDA, Tomotake, et al. *Critical role of peroxisome proliferator-activated receptor γ on anoikis and invasion of squamous cell carcinoma*. Clinical Cancer Research, 2005, vol. 11, no 11, p. 4012-4021).

In hematopoietic cancer model systems, initial screening showed that several myeloma (MM) as non-Hodgkin lymphoma (NHL) cell lines had the greatest sensitivity to the antiproliferative effects of the antagonists, GW9662 and T0070907. (BURTON, Jack D., et al. *Peroxisome proliferator-activated receptor-γ antagonists exhibit potent antiproliferative effects versus many hematopoietic and epithelial cancer cell lines*. Anti-cancer drugs, 2007, vol. 18, no 5, p. 525-534.)

Other study demonstrates that silencing PPAR-gamma expression by RNAi in human Burkitt's type B lymphoma cells increased basal and mitogen-induced proliferation and survival. These cells also had increased survival upon exposure to PPAR-gamma ligands and exhibited a less differentiated phenotype. (GARCIA-BATES, Tatiana M., et al. *Peroxisome proliferator-activated receptor gamma overexpression and knockdown: impact on human B cell lymphoma proliferation and survival*. Cancer immunology, immunotherapy, 2009, vol. 58, no 7, p. 1071-1083).

Other study suggests that a combination therapy using PPAR-gamma ligands and its inhibitor, GW9662, could be a potential therapeutic strategy targeting glioblastoma stem cells. (IM, Chang-Nim. *Combination Treatment with PPARγ Ligand and Its Specific Inhibitor GW9662 Downregulates BIS and 14-3-3 Gamma, Inhibiting Stem-Like Properties in Glioblastoma Cells*. BioMed Research International, 2017, vol. 2017).

PPAR-Gamma and Metabolic Diseases

Seminal studies in vitro have demonstrated that this receptor is both necessary and sufficient for adipocyte differentiation, and that it promotes lipid accumulation by adipocytes. It is known that the anti-diabetic thiazolidinedione (TZD) family which are PPAR-gamma agonists, suppress insulin resistance in adipose tissue in addition to in skeletal muscle and liver, which contain low concentrations of PPAR-gamma. Consonant with this, it has been demonstrated that they alter the expression of genes that are involved in lipid uptake, lipid metabolism and insulin action in adipocytes. Data from patients with type 2 diabetes mellitus (T2DM) and preclinical species also demonstrate that PPAR-gamma agonists function as 'adipose remodeling factors' that redistribute lipids from insulin-resistant, lipolytic visceral-fat depots into subcutaneous fat that contains small, newly differentiated, insulin-responsive adipocytes (BERGER, Joel P.; AKIYAMA, Taro E.; MEINKE, Peter T. *PPARs: therapeutic targets for metabolic disease*. Trends in pharmacological sciences, 2005, vol. 26, no 5, p. 244-251, and its references).

Atherosclerosis

PPAR-gamma is also expressed at relatively high levels in various vascular cells, including endothelial cells, smooth muscle cells and monocyte/macrophages. PPAR-gamma agonists have been reported to attenuate atherosclerosis in genetically prone mouse models: LDLR$^{-/-}$ and the ApoE$^{-/-}$ or intimal to medial ratio in human patients. In another study, troglitazone treatment of male LDLR$^{-/-}$ mice previously maintained on a HFD or high-fructose diet significantly reduced atherosclerotic lesions. (HAN, Lu, et al. *PPARs: regulators of metabolism and as therapeutic targets in cardiovascular disease. Part II: PPAR-β/δ and PPAR-γ*. Future cardiology, 2017). Other study shown that administration of PPAR-gamma activators decreases the size of atherosclerotic lesions in low-density lipoprotein receptor knockout (LDLRK/K) (LI, Andrew C., et al. *Peroxisome proliferator-activated receptor γ ligands inhibit development of atherosclerosis in LDL receptor-deficient mice*. The Journal of clinical investigation, 2000, vol. 106, no 4, p. 523-531). This anti-atherogenic activity occurs independently of improvements in dyslipidemia, insulin resistance and hypertension, which indicates direct vascular effects; as a result PPAR-gamma agonists also exert a broad spectrum of antiatherogenic effects in vitro and in animal models of atherosclerosis (HSUEH, Willa A.; BRUEMMER, Dennis. *Peroxisome proliferator-activated receptor γ: implications for cardiovascular disease*. Hypertension, 2004, vol. 43, no 2, p. 297-305.).

PPAR-Gamma Regulation of Metabolic Functions in Liver, Skeletal Muscle & Heart

In contrast to adipose tissue, liver, skeletal muscle and heart express PPAR-gamma protein only at low-to moderate levels. However, under certain pathophysiologic conditions, the expression of PPAR-gamma protein is significantly upregulated in these tissues. Several studies have provided evidence that expression of hepatic PPAR-gamma is markedly upregulated in many models of obesity (both lipoatrophy and hyperphagic obesity), insulin resistance and diabetes with varying degree of steatosis. (NEUSCHWANDER-TETRI, Brent A., et al. *Improved nonalcoholic steatohepatitis after 48 weeks of treatment with the PPAR-γ ligand rosiglitazone*. Hepatology, 2003, vol. 38, no 4, p. 1008-1017.), Likewise, increased expression of hypoxia-inducible factor (HIF-1α) and PPAR-gamma is reported in ventricular biopsy samples of humans and mice with hypertrophic cardiomyopathy (KRISHNAN, Jaya, et al. *Activation of a HIF1α-PPARγ axis underlies the integration of glycolytic and lipid anabolic pathways in pathologic cardiac hypertrophy*. Cell metabolism, 2009, vol. 9, no 6, p. 512-524.). Further evaluation of mouse samples revealed that HIF-1α caused the induction of PPAR-gamma gene expression, and subsequently lead to cardiac steatosis, apoptosis and heart failure (KINTSCHER, Ulrich; LAW, Ronald E. *PPARγ-mediated insulin sensitization: the importance of fat versus muscle*. American Journal of Physiology-Endocrinology And Metabolism, 2005, vol. 288, no 2, p. E287-E291).

In addition it has been reported that PPAR-gamma gene expression is upregulated in skeletal muscle of obese subjects with T2DM (PARK, Kyong Soo, et al. *PPAR-γ gene expression is elevated in skeletal muscle of obese and type II diabetic subjects*. Diabetes, 1997, vol. 46, no 7, p. 1230-1234.).

Inflammation, Hypertension and Vasculature

PPAR-gamma ligands have also been shown to inhibit the production of many inflammatory mediators and cytokines in various cell types, including monocytes/macrophages, epithelial cells, smooth muscle cells, endothelial cells, dendritic cells and lymphocytes (reviewed in [DAYNES, Raymond A.; JONES, Dallas C. *Emerging roles of PPARs in inflammation and immunity*. Nature reviews. Immunology, 2002, vol. 2, no 10, p. 748., KOSTADINOVA, Radina; WAHLI, Walter; MICHALIK, Liliane. *PPARs in diseases: control mechanisms of inflammation*. Current medicinal chemistry, 2005, vol. 12, no 25, p. 2995-3009). In addition, PPAR-gamma ligands have been shown to have anti-inflammatory effects in several disease models including atherosclerosis, obesity-induced insulin resistance, allergic encephalomyelitis, Parkinson, Alzheimer, psoriasis, inflammatory bowel diseases, and arthritis. (RICOTE, Mercedes; GLASS, Christopher K. *PPARs and molecular mechanisms of transrepression*. Biochimica et Biophysica Acta (BBA)-Molecular and Cell Biology of Lipids, 2007, vol. 1771, no 8, p. 926-935., and its references).

Concerning to the effect of PPAR-gamma against hypertension, a genetic analysis shows that 2 dominant negative mutations in PPAR-gamma are associated with severe hypertension in humans, indicating an important role of PPAR-gamma in blood pressure regulation. PPAR-gamma agonists lower blood pressure in diabetic mice (RYAN, Michael J., et al. *PPARγ agonist rosiglitazone improves vascular function and lowers blood pressure in hypertensive transgenic mice*. Hypertension, 2004, vol. 43, no 3, p. 661-666).

PPAR-gamma agonists exhibit potent anti-inflammatory effects and have direct neuroprotective actions. PPAR-gamma agonists have been shown to be efficacious in animal models of Alzheimer's disease, stroke, multiple sclerosis, Parkinson's disease and amyotrophic lateral sclerosis. (SUNDARARAJAN, Sophia, et al. *PPARγ as a therapeutic target in central nervous system diseases*. Neurochemistry international, 2006, vol. 49, no 2, p. 136-144, and its references).

Cardiovascular Diseases

It is known that PPAR-gamma agonists confer benefits in diabetes and atherosclerosis, which are known risk factors associated with cardiovascular disease. Preclinical studies have shown that pharmacological modulation of PPARs can upregulate the expression of fatty acid oxidation genes in cardiomyocytes. Moreover, PPAR agonists were proven able to improve ventricular contractility and reduce cardiac remodeling in animal models through their anti-inflammatory, anti-oxidant, anti-fibrotic, and anti-apoptotic activities. (ABUSHOUK, Abdelrahman Ibrahim, et al. *Peroxisome proliferator-activated receptors as therapeutic targets for heart failure*. Biomedicine & Pharmacotherapy, 2017, vol. 95, p. 692-700).

Immunotherapy

It is known that PPAR-gamma antagonists act as negative regulators of T cells in addition to their inhibition of bone marrow (BM) adipogenesis. This hold implications for the application of PPAR-gamma antagonists in immune-mediated pathophysiologies both in the laboratory and in the clinic. (SATO, Kazuya, et al. *PPARγ antagonist attenuates mouse immune-mediated bone marrow failure by inhibition of T cell function*. haematologica, 2016, vol. 101, no 1, p. 57-67.)

From other study, it is known that PPAR-gamma-deficient T cells are hyper-reactive to TCR stimulation. Various cytokines including IFN-c, IL-4, IL-17, and IL-2 were increased in PPAR-gamma-deficient T cells compared to littermate control T cells, suggesting that these cells are hyper-reactive to TCR stimulation. In addition, PPAR-gamma-deficient T cells proliferated significantly more than control CD4+ T cells, suggesting that PPAR-gamma plays a role as a negative regulator of T cell activation and proliferation. (PARK, Hong-Jai, et al. *PPARγ negatively regulates T cell activation to prevent follicular helper T cells and germinal center formation*. PloS one, 2014, vol. 9, no 6, p. e99127).

On the other hand, it has been reported that decreasing PPAR-gamma activity, either by treatment with PPAR-gamma antagonist or by invalidation of one allele of the PPAR-gamma gene, leads to a reduction of both high fat diet-induced adipocyte hypertrophy and insulin resistance. Treatment with PPAR-gamma antagonist also dramatically improves insulin sensitivity in the diabetic mice. Thus, demonstrating both antiobesity and antidiabetic effect. (EUSSET, Jennifer, et al. *A new selective peroxisome proliferator-activated receptor γ antagonist with antiobesity and antidiabetic activity*. Molecular Endocrinology, 2002, vol. 16, no 11, p. 2628-2644).

Data from human genetic studies and from PPAR-gamma heterozygous knockout mice indicate that a reduction in PPAR-gamma activity could paradoxically improve insulin sensitivity. These findings suggest that modulation of PPAR-gamma activity by partial agonists or compounds that affect cofactor recruitment might hold promise for the treatment of insulin resistance.

On the other hand, there is genetic evidence that reducing the activity of peroxisome proliferation receptor-gamma (PPAR-gamma) may increase insulin sensitivity. (DOGGRELL, Sheila. *Do peroxisome proliferation receptor-γ antagonists have clinical potential as combined antiobesity and antidiabetic drugs?*. Expert opinion on investigational drugs, 2003, vol. 12, no 4, p. 713-716).

It has been shown that PPAR-gamma antagonist functions to form bone tissue and is effective, for example, as a therapeutic agent for osteoporosis and the like. (DUQUE, Gustavo, et al. *Pharmacological inhibition of PPARγ increases osteoblastogenesis and bone mass in male C57BL/6 mice*. Journal of Bone and Mineral Research, 2013, vol. 28, no 3, p. 639-648).

Hence, the problem to be solved by the present invention is to provide compounds as modulator of PPAR-gamma receptor, and more particularly as antagonist of PPAR-gamma receptor.

The authors of the present invention have developed new benzamide derivatives conveniently substituted as potent modulator of PPAR-gamma receptor.

SUMMARY OF THE INVENTION

In a first aspect (aspect 1), the present invention refers to new benzamide derivatives of formula (I):

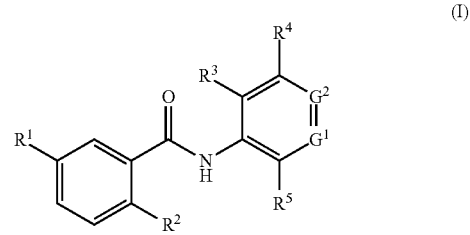

wherein:

R² is selected from Cl and F atoms,

R¹ represents a cyano group,

G¹ and G² independently represent a group selected from N atom and —CR⁹ wherein G¹ and G² are not simultaneously CR⁹, R⁹ is independently selected from the group consisting of:
- a) five or a six-membered heteroaryl ring optionally substituted by one or more substituents selected from the group consisting of halogen atom, cyano group, —COOH group, linear or branched $C_1$-$C_3$ alkyl group, linear or branched $C_1$-$C_3$ alkoxy, linear or branched $C_1$-$C_3$ haloalkyl group, $C_3$-$C_4$ cycloalkyl, and $C_3$-$C_4$ cycloalkoxy,
- b) phenyl group optionally substituted by one or more substituents selected from the group consisting of halogen atom, cyano group, —COOH group, linear or branched $C_1$-$C_3$ alkyl group, linear or branched $C_1$-$C_3$ alkoxy, linear or branched $C_1$-$C_3$ haloalkyl group, $C_3$-$C_4$ cycloalkyl, $C_3$-$C_4$ cycloalkoxy,
- c) a five or six-membered saturated heterocyclic ring comprising one or two heteroatoms selected from N and O as part of the cycle, which heterocycle is optionally substituted by a group selected from $C_1$-$C_3$ alkyl group, and $C_3$-$C_4$ cycloalkyl group, and
- d) —$C_3$-$C_6$ cycloalkyl group.

R³, R⁴ and R⁵ are independently selected from the group consisting of hydrogen atom, halogen atom, linear or branched $C_1$-$C_3$ alkyl group, $C_3$-$C_4$ cycloalkyl group and cyano group, and pharmaceutically acceptable salts thereof.

Other aspects of the present invention are:

Aspect 2) processes for the preparation of the compounds of aspect 1,

Aspect 3) pharmaceutical compositions comprising a therapeutically effective amount of a compound of aspect 1, Aspect 4) pharmaceutical compositions according to aspect 3 further comprising a therapeutically effective amount of chemotherapeutics agents, anti-inflammatory agents, steroids, immunotherapeutic agent and other agents such as therapeutic antibodies.

Aspect 5) Compounds of aspect 1 for use in the treatment of diseases that can be ameliorated by modulation of PPAR-gamma receptor.

Aspect 6) Methods for the treatment of diseases that can be ameliorated by modulation of PPAR-gamma receptor by administration of the compounds of aspect 1 or the pharmaceutical compositions of aspects 3 or 4 to a subject in need of said treatment, wherein said diseases may be selected from the group consisting of cancer selected from breast cancer, pancreatic cancer, ovarian cancer, prostate cancer, renal cancer, bladder cancer, testicular cancer, urothelial cancer skin cancer, melanoma, colon cancer, kidney cancer, brain cancer or a hematopoietic cancer selected from lymphoma, multiple myeloma and leukemia; metabolic diseases selected from osteoporosis, rachitis, arthrosis, obesity, type I and type II diabetes mellitus, lipid metabolism disorder, pancreatitis, glucose metabolism disorder, diabetic neuropathy, diabetic complications, hyperuricemia, osteoporosis, rachitis, arthrosis inflammatory diseases such as inflammatory skin diseases selected from psoriasis, atopic dermatitis, eczema, acne vulgaris, other dermatitides and pruritu, pulmonary disorders selected from asthma, and chronic obstructive pulmonary disease, autoimmune disease, neurodegenerative disease selected from multiple sclerosis, Alzheimer's disease, Parkinson's disease, cardiovascular diseases selected from atherosclerosis, venous and arterial occlusive diseases, restenosis after invasive procedures, cardiomyopathy, myocardial fibrosis, congestive heart failure, angiogenesis and neovascularization in neoplastic diseases and renal diseases.

Aspect 7) combination products comprising a compound of formula (I) or a pharmaceutically acceptable salt thereof and one or more therapeutic agents selected from the group consisting of chemotherapeutics agents, anti-inflammatory agents, steroids, immunosuppressants, therapeutic antibodies, that can be used in combination with the compounds of the present application for treatment of f diseases, disorders or conditions associated with the modulation of PPAR-gamma receptor. The one or more additional pharmaceutical agents can be administered to a patient simultaneously or sequentially.

Example chemotherapeutics agents include proteosome inhibitors (e.g., bortezomib), chemotherapeutics agents for treatment of CNS cancer including temozolomide, carboplatin, carmustine (BCNU), cisplatin, cyclophosphamide, etoposide, irinotecan, lomustine (CCNU), methotrexate, procarbazine, vincristine, and other chemotherapeutics agents such as thalidomide, revlimid, and DNA-damaging agents such as melphalan, doxorubicin, cyclophosphamide, vincristine, etoposide, carmustine, and the like.

Example anti-inflammatory compounds include aspirin, choline salicylates, celecoxib, diclofenac potassium, diclofenac sodium, diclofenac sodium with misoprostol, diflunisal, etodolac, fenoprofen, flurbiprofen, ibuprofen, ketoprofen, meclofenamate sodium, mefenamic acid, nabumetone, naproxen, naproxen sodium, oxaprozin, piroxican, rofecoxib, salsalate, sodium salicylate, sulindac, tolmetin sodium, valdecoxib, and the like.

Example steroids include corticosteroids such as cortisone, dexamethasone, hydrocortisone, methylprednisolone, prednisolone, prednisone, and the like.

Example immunosuppressants include azathioprine, chlorambucil, cyclophosphamide, cyclosporine, daclizumab, infliximab, methotrexate, tacrolimus, and the like.

Example of therapeutic antibodies for use in combination therapy include but are not limited to trastuzumab (e.g. anti-HER2), ranibizumab (e.g. anti-VEGF-A), bevacizumab (e.g. anti-VEGF), panitumumab (e.g. anti-EGFR), cetuximab (e.g. anti-EGFR), rituxan (anti-CD20) and antibodies directed to c-MET.

In still another aspect the present invention relates to a combination product comprising compound of formula (I) or a pharmaceutically acceptable salt thereof and one or more immunotherapeutic agent useful in the treatment of cancer, selected from breast cancer, pancreatic cancer, ovarian cancer, bladder cancer, prostate cancer, renal cancer, testicular cancer, urothelial cancer skin cancer, melanoma, colon cancer, kidney cancer, brain cancer or a hematopoietic cancer selected from lymphoma, multiple myeloma and leukemia.

In a preferred embodiment, a combination product comprises a compound of formula (I) or a pharmaceutically acceptable salt thereof, and one or more immunotherapeutic agent selected from the group consisting of antibodies anti-CTLA4, such as Ipilimumab and Tremelimumab, antibodies anti-PD1 such as MDX-1106 (nivolumab), MK3475 (pembrolizumab), CT-011 (pidilizumab), PDR001 and AMP-224 and antibodies anti-PDL1 such as MPDL3280A (Atezolizumab), Avelumab (MSB0010718C), Durvalumab (MEDI4736) and MDX-1105, and monoclonal antibody that targets glycolipid GD2 as Dinutuximab. The components of the combination product are in the same formulation or in separate formulations.

In another possible embodiment, a combination product comprises a PPAR-γ activator selected from rosiglitazone and pioglitazone. These drugs arrest cancer cells in the GI phase of the cell cycle and may not cause this effect through PPAR-gamma-dependent actions. The PPAR-gamma-independent effects of the activators and the PPAR-gamma-dependent effects of the antagonists used together could be synergistic.

Accordingly, the derivatives of the present invention and pharmaceutically acceptable salts and pharmaceutical compositions comprising such compounds and/or salts thereof, may be used in a method of treatment of pathological conditions or disease of human body which comprises administering to a subject in need of said treatment, an effective amount of the benzamide derivatives of the invention or a pharmaceutically acceptable salt thereof.

As it is said before, the benzamide derivatives of the present invention are useful in the treatment or prevention of diseases known to be susceptible to amelioration by treatment with a modulator of PPAR-gamma receptor. Such diseases are selected from cancer selected from breast cancer, pancreatic cancer, ovarian cancer, prostate cancer, renal cancer, bladder cancer, testicular cancer, urothelial cancer skin cancer, melanoma, colon cancer, kidney cancer, brain cancer or a hematopoietic cancer selected from lymphoma, multiple myeloma and leukemia; metabolic diseases selected from osteoporosis, rachitis, arthrosis, obesity, type I and type II diabetes mellitus, lipid metabolism disorder, pancreatitis, glucose metabolism disorder, diabetic neuropathy, diabetic complications, hyperuricemia, osteoporosis, rachitis, arthrosis inflammatory diseases such as inflammatory skin diseases selected from psoriasis, atopic dermatitis, eczema, acne vulgaris, other dermatitides and pruritu, pulmonary disorders selected from asthma, and chronic obstructive pulmonary disease, autoimmune disease, neurodegenerative disease selected from multiple sclerosis, Alzheimer's disease, Parkinson's disease, cardiovascular diseases selected from atherosclerosis, venous and arterial occlusive diseases, restenosis after invasive procedures, cardiomyopathy, myocardial fibrosis, congestive heart failure, angiogenesis and neovascularization in neoplastic diseases and renal diseases.

As used herein, the term halogen atom comprises chlorine, fluorine, bromine or iodine atom, preferably fluorine, chlorine or bromine atom. The term halo when used as a prefix has the same meaning.

As used herein, the term $C_1$-$C_3$ haloalkyl is used to designate $C_1$-$C_3$ alkyl substituted by one or more halogen atoms, preferably one, two or three halogen atoms. Preferably, the halogen atoms are selected from the group consisting of fluorine or chlorine atoms. In a preferred embodiment, the haloalkyl groups are $C_1$ alkyl substituted by three fluorine atoms (trifluoromethyl group).

As used herein the term $C_1$-$C_3$ alkyl is used to designate linear or branched hydrocarbon radicals ($C_nH_{2n+1}$) having 1 to 3 carbon atoms. Examples include methyl, ethyl, n-propyl, i-propyl radicals.

As used herein, the term $C_n$-$C_m$ cycloalkyl embraces hydrocarbon monocyclic groups having n to m carbon atoms, for example 3 to 6 or 3 to 4 carbon atoms. Such cycloalkyl groups include, by way of example, cyclopropyl, cyclobutyl, cyclopentyl and cyclohexyl.

As used herein, the term $C_1$-$C_3$ alkoxy is used to designate radicals which contain a linear or branched $C_1$-$C_3$ alkyl group linked to an oxygen atom ($C_nH_{2n+1}$—O—). Preferred alkoxy radicals is methoxy.

As used herein the term $C_3$-$C_4$ cycloalkoxy is used to designate radicals containing a $C_3$-$C_4$ cycloalkyl groups linked to an oxygen atom.

As used herein, the terms five to six-membered heteroaryl ring is used to designate an heteroaromatic ring containing carbon, hydrogen and one or more heteroatoms selected from N, O and S as part of the ring such as furan, pyridine, pyrazine, pyrrole, imidazole, pyrazole, oxazole, thiazole and thiophene. Said radicals may optionally be substituted by one or more substituents according to have been defined in each case. The preferred radicals are optionally substituted pyridyl, pyrimidinyl. When a heteroaryl radical carries two or more substituents, the substituents may be the same or different.

As used herein, the term five or six-membered saturated heterocycle rig is used to designate saturated heterocyclic ring containing carbon, hydrogen and one or more heteroatoms selected from N and O as part of the ring such as pyrrolidinyl, tetrahydrofuranyl, dioxolanyl, pyrazolidinyl, imidazolinyl, piperazinyl, piperidinyl and morpholinyl. Said radicals may optionally be substituted by one or more substituents according to have been defined in each case. The preferred radicals are optionally substituted piperidinyl, piperazinyl and morpholinyl. When heterocyclic radical carries 2 or more substituents, the substituents may be the same or different.

As used herein, some of the atoms, radicals, chains or cycles present in the general structures of the invention are "optionally substituted". This means that these atoms, radicals, chains or cycles can be either unsubstituted or substituted in any position by one or more, for example 1, 2, 3 or 4, substituents, whereby the hydrogen atoms bound to the unsubstituted atoms, radicals, chains or cycles are replaced by chemically acceptable atoms, radicals, chains or cycles. When two or more substituents are present, each substituent may be the same or different As used herein, the term pharmaceutically acceptable salt is used to designate salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium), alkali earth metal (e.g. calcium or magnesium) hydroxides, and organic bases, for example alkyl amines, arylalkyl amines and heterocyclic amines.

Other preferred salts according to the invention are quaternary ammonium compounds wherein an equivalent of an anion ($X^{-n}$) is associated with the positive charge of the N atom. $X^{-n}$ may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and toluenesulphonate. $X^{-n}$ is preferably an anion selected from chloride, bromide, iodide, sulphate, nitrate, acetate, maleate, oxalate, succinate or trifluoroacetate. More preferably, $X^{-n}$ is chloride, bromide, trifluoroacetate or methanesulphonate.

The term "modulator" refers to a molecule such as a compound, a drug, enzyme, or a hormone that blocks or otherwise interferes with a particular biologic activity.

The term "$IC_{50}$", as used herein, refers to concentration causing a half-maximal inhibition of control specific binding. IC$_{50}$ values can be estimated from an appropriate dose-response curve, more accurately, IC$_{50}$ values may be determined using non-linear regression analysis.

According to one embodiment of the present invention R$^3$, R$^4$ and R$^5$ are independently selected from hydrogen atom and halogen atom.

According to one embodiment of the present invention R$^3$, R$^4$ and R$^5$ are hydrogen atoms.

According to one embodiment of the present invention G$^1$ represents a nitrogen atom and G$^2$ represents a —CR$^9$ group, wherein R$^9$ is selected from:
  a) phenyl group optionally substituted by one or more substituents selected from the group consisting of halogen atom, —COOH group,
  b) a pyridyl ring optionally substituted by one or more substituents selected from the group consisting of halogen atom and cyano group,
  c) a morpholinyl and piperazinyl group optionally substituted by a group selected from of C$_1$-C$_3$ alkyl group and C$_3$-C$_6$ cycloalkyl group.

According to another embodiment of the present invention G$^2$ represents a nitrogen atom and G$^1$ represents a —CR$^9$ group, wherein R$^9$ is selected from:
  a) phenyl group optionally substituted by one or more substituents selected from the group consisting of halogen atom and —COOH group,
  b) pyridinyl ring optionally substituted by one or more substituents selected from the group consisting of halogen atom and cyano group,
  c) a morpholinyl and piperazinyl groups optionally substituted by a group selected from of C$_1$-C$_3$ alkyl group and C$_3$-C$_6$ cycloalkyl group.

In other embodiment of the present invention, R$^1$ represents a cyano group, R$^3$, R$^4$ and R$^5$ represent hydrogen atoms, G$^1$ represents a N atom and G$^2$ represents a —CR$^9$ group, wherein R$^9$ represents a phenyl group optionally substituted by one or more substituents selected from the group consisting of halogen atom, —COOH group and cyano group.

In other embodiment of the present invention, R$^1$ represents a cyano group, R$^3$, R$^4$ and R$^5$ independently represent a hydrogen atom, G$^1$ represents a N atom and G$^2$ represents a —CR$^9$ group, wherein R$^9$ represents pyridyl ring optionally substituted by one or more substituents selected from the group consisting of halogen atom, cyano group.

In another preferred embodiment, R$^1$ represents a cyano group, R$^3$, R$^4$ and R$^5$ independently represent a hydrogen atom, G$^1$ represents a N atom and G$^2$ represents a —CR$^9$ group, wherein R$^9$ represents pyridyl ring optionally substituted by one or more substituents selected from the group consisting of halogen atom, cyano group.

In another preferred embodiment, R$^1$ represents a cyano group, R$^3$, R$^4$ and R$^5$ represents hydrogen atoms, G$^2$ represents a N atom and G$^1$ represents a —CR$^9$ group, wherein R$^9$ is selected from:
  a) a phenyl group optionally substituted by one or more substituents selected from the group consisting of halogen atom, —COOH group and cyano group,
  b) pyridyl ring optionally substituted by one or more substituents selected from the group consisting of halogen atom, cyano group, Particular individual compounds of the present invention include:
2-chloro-5-cyano-N-(2-phenylpyridin-4-yl)benzamide
2-chloro-5-cyano-N-(6-phenylpyridin-3-yl)benzamide
2-chloro-5-cyano-N-(2-(4-fluorophenyl)pyridin-4-yl)benzamide
2-chloro-5-cyano-N-(6-(4-fluorophenyl)pyridin-3-yl)benzamide
N-([2,3'-bipyridin]-5-yl)-2-chloro-5-cyanobenzamide
N-([2,3'-bipyridin]-4-yl)-2-chloro-5-cyanobenzamide
N-([2,4'-bipyridin]-5-yl)-2-chloro-5-cyanobenzamide
N-([2,4'-bipyridin]-4-yl)-2-chloro-5-cyanobenzamide
N-([2,3'-bipyridin]-5-yl)-5-cyano-2-fluorobenzamide
5-cyano-2-fluoro-N-(6-(4-fluorophenyl)pyridin-3-yl)benzamide
5-cyano-2-fluoro-N-(2-(4-fluorophenyl)pyridin-4-yl)benzamide
N-([2,3'-bipyridin]-4-yl)-5-cyano-2-fluorobenzamide
N-([2,2'-bipyridin]-5-yl)-2-chloro-5-cyanobenzamide
2-chloro-5-cyano-N-(6-(4-methylpiperazin-1-yl)pyridin-3-yl)benzamide
2-chloro-5-cyano-N-(2-(4-methylpiperazin-1-yl)pyridin-4-yl)benzamide
2-chloro-5-cyano-N-(2-morpholinopyridin-4-yl)benzamide
2-chloro-5-cyano-N-(6-morpholinopyridin-3-yl)benzamide
N-([2,4'-bipyridin]-4-yl)-5-cyano-2-fluorobenzamide
N-([2,4'-bipyridin]-5-yl)-5-cyano-2-fluorobenzamide
2-chloro-5-cyano-N-(pyridazin-4-yl)benzamide
5-cyano-2-fluoro-N-(pyridazin-4-yl)benzamide
2-chloro-5-cyano-N-(6-cyclopropylpyridin-3-yl)benzamide
3-(5-(2-chloro-5-cyanobenzamido)pyridin-2-yl)benzoic acid
4-(5-(2-chloro-5-cyanobenzamido)pyridin-2-yl)benzoic acid The compounds of this invention can be prepared by using the procedures described below. To facilitate the description of the procedures, concrete examples have been used but they do not restrict in any way the scope of the present invention.

The synthesis of compound of formula (I) is outlined in the following schemes.

Scheme 1

In Scheme 1 the synthesis of intermediate compounds of formula (III) and compounds of formula (I) are described

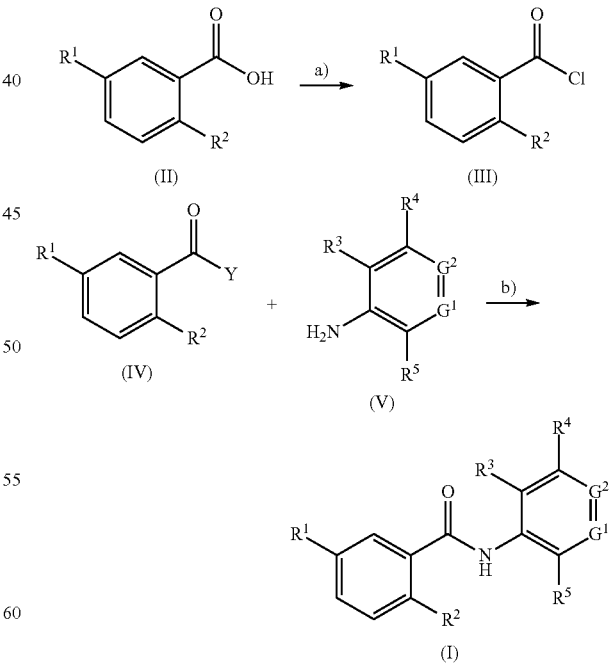

Reagents and condition: a) SOCl$_2$; b) Y = Cl or OH; (Y = Cl), TEA, DMAP, Acetonitrile, 40° C.; (Y = OH), HATU, DIPEA, DCM/EDC, Piridine, 60° C.

The amines of formula (V) can be acylated using either the carboxylic acid of formula (II) or an acyl chloride derivative of formula (III), where $R^1$ was defined above, giving the amide derivatives of formula (I) which are particular cases of compounds claimed by the present invention. The commercially available acids of formula (II) are reacted with thionyl chloride to afford the acyl chloride of formula (III). For the preparation of the amides of formula (I) with the carboxylic acid of formula (II), the acid is activated with typical coupling reagent such as HATU, EDC, in the presence of a base such as triethyl amine or DIPEA with the corresponding heteroaryl amine of formula (IV) at room temperature.

Scheme 2

In Scheme 2 the synthesis of intermediate compounds of formula (IX) and (X) are described

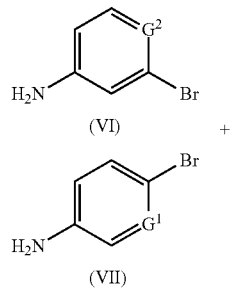

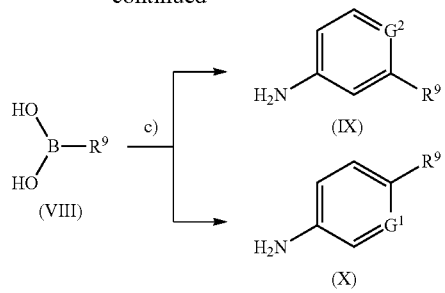

Reagents and conditions: c) [1,1'-Bis(diphenylphosphino)efffocene] dichloropalladimu(II), $Cs_2CO_3$, 1,4-Dioxane/$H_2O$, 100° C., 12 h.

The synthesis of the amines of formula (IX) and (X), which are particular cases of the amines of formula (V), is carried out by a Suzuki-type coupling of the heteroaryl amine of formula (VI) or (VII) with boronic acid or boronate derivatives of $R^9$ using a palladium catalyst such as [1,1'-Bis(diphenylphosphino)ferrocene]dichloropalladium(II), complex with dichloromethane in dioxane in the presence of an aqueous solution of a base such as cesium carbonate and at temperature between 25° C. ant 110° C.

Scheme 3

In Scheme 3 the synthesis of intermediate compounds of formula (IX) and (X) are described

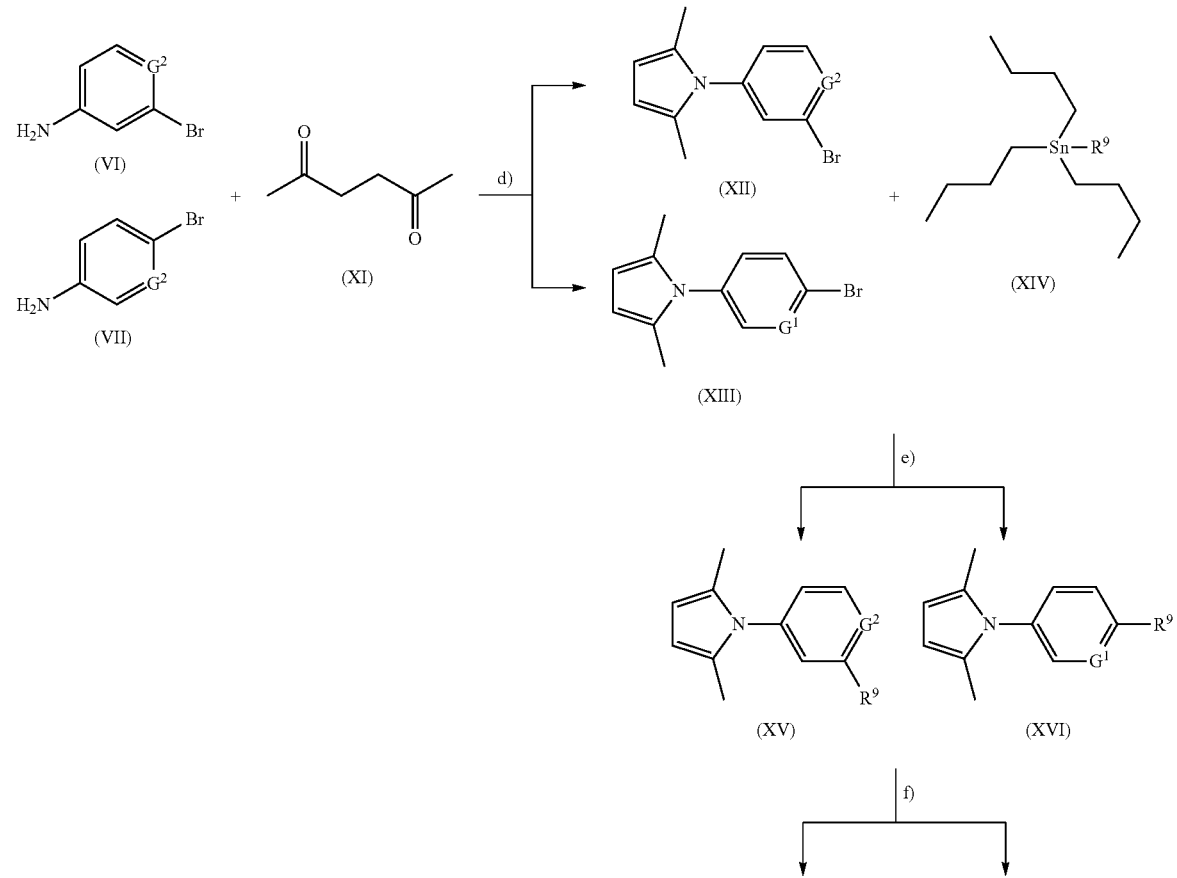

-continued

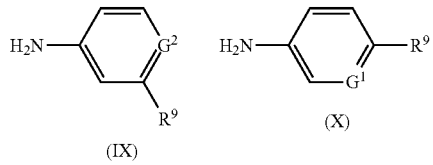

Reagents and conditions: d) molecular sieves, p-toluensulphonic acid, toluene, 4 h at reflux; e) tetrakis(triphenylphosphine)palladium, toluene, N₂, 130° C. overnight; f) hydroxylamine hydrochloride, triethylamine, ethanol/H₂O, 80° C., 20 h.

Tributylstannyl derivatives are used to introduce the $R^9$ substituent in some particular cases. The reaction is carried out under $N_2$ atmosphere, tetrakis(triphenylphosphine)palladium as catalyst, in dry toluene at 130° C. overnight. The amino group is protected before by the reaction with hexane-2,5-dione (XI) and formation of the 2,5-dimethyl-1H-pyrrol derivative (XII) or (XIII). The amino group was released again with hydroxylamine in the presence of triethylamine in an ethanol water solution at 80° C. for 20 hours to provide the intermediates of formula (IX) or (X).

Scheme 4

In Scheme 4 the synthesis of intermediate compounds of formula (IX) and (X) are described

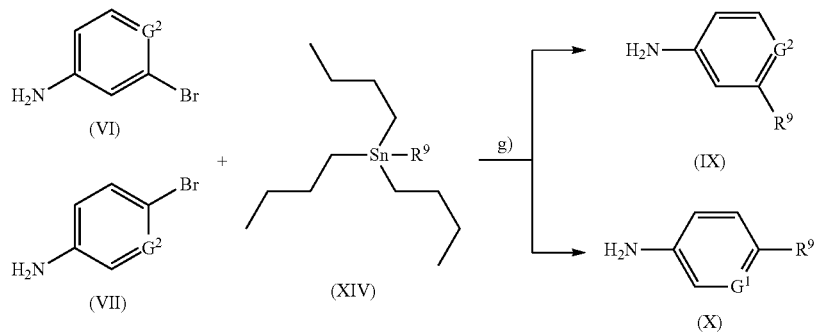

Reagents and conditions: g) tetrakis(triphenylphosphine)palladium, toluene, N₂, 130° C., 48 h.

It is also possible to carry out the reaction without the amino protective group. In this case, the heteroaryl amines of formula (VI) or (VII) react with tributylstannyl derivatives under $N_2$ atmosphere, tetrakis(triphenylphosphine)palladium as catalyst, in dry toluene at 130° C. for 48 h, namely with good yield.

Abbreviations

In the present application are used the following abbreviations with the corresponding Definitions RT: Room temperature
Pd₂(dba)₃: Tris(dibenzylideneacetone)dipalladium
SPhos: dicyclohexyl(2',6'-dimethoxy-[1,1'-biphenyl]-2-yl)phosphine
TEA: Triethylamine
NaHMDS: Sodium bis(trimethylsilyl)amide
THF: Tetrahydrofuran
DMSO: Dimethyl sulfoxide
Pharmacological Activity Results The compounds of the present invention were assayed for binding to the Human PPAR-gamma (h) (agonist radioligand) Assay and were tested at several concentrations for IC50 determination.

Compound binding was calculated as a % inhibition of the binding of a radioactively labelled ligand specific for each target, as described in (FERRY, Gilles, et al. *Binding of prostaglandins to human PPARγ: tool assessment and new natural ligands*. European journal of pharmacology, 2001, vol. 417, no 1, p. 77-89).

The $IC_{50}$ values (concentration causing a half-maximal inhibition of control specific binding) was determined by non-linear regression analysis of the competition curves generated with mean replicate values using Hill equation curve fitting $$Y = D + \left[\frac{A - D}{1 + (C/C_{50})^{nH}}\right]$$

where Y=specific binding, A=left asymptote of the curve, D=right asymptote of the curve, C=compound concentration, C50=IC50, and nH=slope factor. This analysis was performed using software developed at EUROFINS Cerep Company (Hill software) and validated by comparison with data generated by the commercial software SigmaPlot® 4.0 for Windows® (© 1997 by SPSS Inc.).

The inhibition constants (Ki) were calculated using the Cheng Prusoff equation $$K_i = \frac{IC_{50}}{(1 + L/K_D)}$$

where L=concentration of radioligand in the assay, and KD=affinity of the radioligand for the receptor. A scatchard plot is used to determine the KD.

Table 1 shows the $IC_{50}$ values of some compounds of the present invention.

$IC_{50}$ Ranges: A<0.2 µM; 0.2 µM<=B<1 µM; 1 µM<=C<50 µM m, D>=50 µM.

TABLE 1

| Example No. | IUPAC Name | IC50 (nM) |
|---|---|---|
| 1 | 2-chloro-5-cyano-N-(2-phenylpyridin-4-yl)benzamide | A |
| 2 | 2-chloro-5-cyano-N-(6-phenylpyridin-3-yl)benzamide | A |
| 3 | 2-chloro-5-cyano-N-(2-(4-fluorophenyl)pyridin-4-yl)benzamide | B |
| 4 | 2-chloro-5-cyano-N-(6-(4-fluorophenyl)pyridin-3-yl)benzamide | A |
| 5 | N-([2,3'-bipyridin]-5-yl)-2-chloro-5-cyanobenzamide | A |
| 6 | N-([2,3'-bipyridin]-4-yl)-2-chloro-5-cyanobenzamide | C |
| 7 | N-([2,4'-bipyridin]-5-yl)-2-chloro-5-cyanobenzamide | C |
| 9 | N-([2,3'-bipyridin]-5-yl)-5-cyano-2-fluorobenzamide | A |
| 10 | 5-cyano-2-fluoro-N-(6-(4-fluorophenyl)pyridin-3-yl)benzamide | A |
| 13 | N-([2,2'-bipyridin]-5-yl)-2-chloro-5-cyanobenzamide | A |
| 14 | 2-chloro-5-cyano-N-(6-(4-methylpiperazin-1-yl)pyridin-3-yl)benzamide | C |
| 15 | 2-chloro-5-cyano-N-(2-(4-methylpiperazin-1-yl)pyridin-4-yl)benzamide | D |
| 16 | 2-chloro-5-cyano-N-(2-morpholinopyridin-4-yl)benzamide | C |
| 17 | 2-chloro-5-cyano-N-(6-morpholinopyridin-3-yl)benzamide | C |

As can be seen from the results described in Table 1, the compounds of the present invention were found to be modulator of PPAR-gamma receptor.

The compounds of the invention are useful in the treatment or prevention of diseases known to be susceptible to improvement by modulation of PPAR-gamma receptor. Such diseases are selected from cancer selected from breast cancer, pancreatic cancer, ovarian cancer, prostate cancer, renal cancer, bladder cancer, testicular cancer, urothelial cancer skin cancer, melanoma, colon cancer, kidney cancer, brain cancer or a hematopoietic cancer selected from lymphoma, multiple myeloma and leukemia; metabolic diseases selected from osteoporosis, rachitis, arthrosis, obesity, type I and type II diabetes mellitus, lipid metabolism disorder, pancreatitis, glucose metabolism disorder, diabetic neuropathy, diabetic complications, hyperuricemia, osteoporosis, rachitis, arthrosis inflammatory diseases such as inflammatory skin diseases selected from psoriasis, atopic dermatitis, eczema, acne vulgaris, other dermatitides and pruritu, pulmonary disorders selected from asthma, and chronic obstructive pulmonary disease, autoimmune disease, neurodegenerative disease selected from multiple sclerosis, Alzheimer's disease, Parkinson's disease, cardiovascular diseases selected from atherosclerosis, venous and arterial occlusive diseases, restenosis after invasive procedures, cardiomyopathy, myocardial fibrosis, congestive heart failure?, angiogenesis and neovascularization in neoplastic diseases and renal diseases.

Accordingly, the derivatives of the invention and pharmaceutically acceptable salts thereof and pharmaceutical compositions comprising such compounds and/or salts thereof, may be used in a method of treatment of disorders of the human body which comprises administering to a subject requiring such treatment an effective amount of the benzamide derivatives of the invention or a pharmaceutically acceptable salt thereof.

One therapeutic use of the compounds of the present invention is to treat proliferative diseases or disorders such as cancer. Cancer is selected from breast cancer, pancreatic cancer, ovarian cancer, prostate cancer, renal cancer, bladder cancer, testicular cancer, urothelial cancer skin cancer, melanoma, colon cancer, kidney cancer, brain cancer or a hematopoietic cancer selected from lymphoma, multiple myeloma and leukemia.

One more preferable therapeutic use of the compounds of the present invention is to treat bladder cancer.

The present invention also provides pharmaceutical compositions which comprise, as an active ingredient, at least a benzamide derivatives of formula (I) or a pharmaceutically acceptable salt thereof in association with other therapeutics agents and a pharmaceutically acceptable excipient such as a carrier or diluent. The active ingredient may comprise 0.001% to 99% by weight, preferably 0.01% to 90% by weight of the composition depending upon the nature of the formulation and whether further dilution is to be made prior to application. Preferably, the compositions are made up in a form suitable for oral, topical, nasal, rectal, percutaneous or injectable administration.

The pharmaceutically acceptable excipients, which are admixed with the active compound or salts of such compound, to form the compositions of this invention, are well known per se and the actual excipients used depend inter alia on the intended method of administering the compositions.

Compositions of this invention are preferably adapted for injectable and per os administration. In this case, the compositions for oral administration may take the form of tablets, retard tablets, sublingual tablets, capsules, inhalation aerosols, inhalation solutions, dry powder inhalation, or liquid preparations, such as mixtures, elixirs, syrups or suspensions, all containing the compound of the invention; such preparations may be made by methods well-known in the art.

The diluents, which may be used in the preparation of the compositions, include those liquid and solid diluents, which are compatible with the active ingredient, together with colouring or flavouring agents, if desired. Tablets or capsules may conveniently contain between 2 and 500 mg of active ingredient or the equivalent amount of a salt thereof.

The liquid composition adapted for oral use may be in the form of solutions or suspensions. The solutions may be aqueous solutions of a soluble salt or other derivative of the active compound in association with, for example, sucrose to form syrup. The suspensions may comprise an insoluble active compound of the invention or a pharmaceutically acceptable salt thereof in association with water, together with a suspending agent or flavouring agent.

Compositions for parenteral injection may be prepared from soluble salts, which may or may not be freeze-dried and which may be dissolved in pyrogen free aqueous media or other appropriate parenteral injection fluid.

Effective doses are normally in the range of 2-2000 mg of active ingredient per day. Daily dosage may be administered in one or more treatments, preferably from 1 to 4 treatments, per day.

The present invention will be further illustrated by the following examples. The following are given by way of illustration and do not limit the scope of the invention in any way.

The synthesis of the compounds of the invention is illustrated by the following examples including the preparation of the intermediates, which do not limit the scope of the invention in any way.

EXAMPLES

General. Reagents, solvents and starting products were acquired from commercial sources. The term "concentration" refers to the vacuum evaporation using a Buchi rotavapor. When indicated, the reaction products were purified by "flash" chromatography on silica gel (40-63 μm) with the indicated solvent system. The spectroscopic data were measured in a Varian Mercury 400 spectrometer. The melting points were measured in a Buchi 535 instrument. The HPLC-MS were performed on a Gilson instrument equipped with a Gilson 321 piston pump, a Gilson 864 vacuum degasser, a Gilson 189 injection module, a 1/1000 Gilson splitter, a Gilson 307 pump, a Gilson 170 detector, and a Thermoquest Fennigan aQa detector.

Intermediate 1: 2-chloro-5-cyanobenzoyl chloride

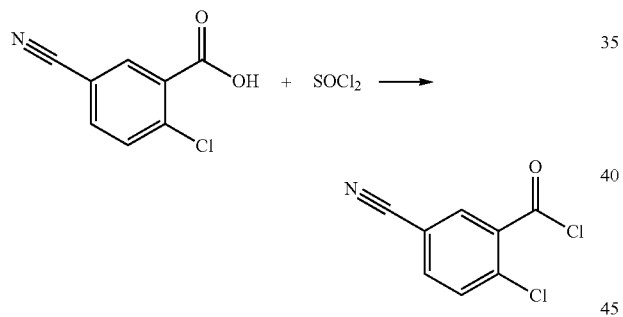

2-chloro-5-cyanobenzoic acid (100 mg, 0.55 mmol) was suspended in 1 mL of thionyl chloride and the reaction mixture was stirred at reflux overnight. The reaction was cooled to room temperature and the solvent was remove under vacuum. The solid was used in the next reaction step without further purification.

The following intermediate was synthesized using the procedure described for the intermediate 1 starting from the 5-cyano-2-fluorobenzoic acid.

Intermediate 2: 5-cyano-2-fluorobenzoyl chloride

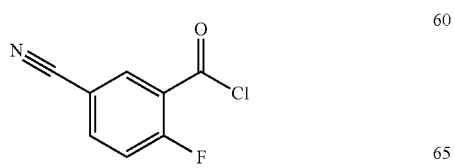

The chloride of the carboxylic acid was also used in the next reaction step without further purification Intermediate 3: 2-phenylpyridin-4-amine

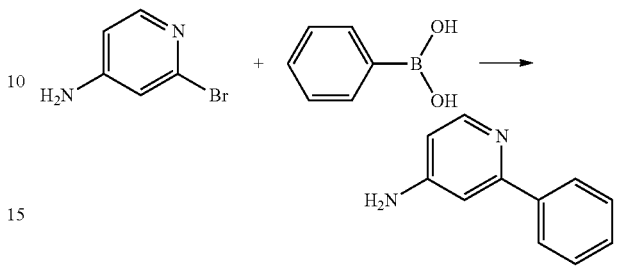

Bromopyridin-4-amine (150 mg, 0.86 mmol), phenylboronic acid (211.4 mg, 1.73 mmol) and [1,1'-Bis(diphenylphosphino)ferrocene]dichloropalladium(II) (42.46 mg, 0.054 mmol) were suspended in a mixture of $Cs_2CO_3$ 2M in water (1.3 mL, 2.60 mmol) and 6.5 mL of 1,4-Dioxane. The reaction mixture was degassed and the vial was sealed and heated at 110° C. overnight. The reaction was quenched with NaOH 1M and extracted two times with ethyl acetate. The organic layer was washed ($NaHCO_3$ saturated and Brine), dried with sodium sulphate and concentrated under vacuum. The crude was purified by CombiFlash column chromatography (Cyclohexane: Ethyl Acetate) to obtain the amine derivative (91.2 mg, 61.8%).

$^1$H-NMR (400 MHz, DMSO-$d_6$): δ=8.08 (d, 1H), 7.90 (d, 2H), 7.44 (t, 2H), 7.37 (t, 1H), 6.99 (d, 1H), 6.45 (dd, 1H), 6.07 (s, 2H).

HPLC-MS: Rt 3.014; m/z 170.9 (MH$^+$).

The following intermediates were synthesized using the procedure described for the intermediate 3 starting from the corresponding pyridinyl halide and boronic acid derivatives.

Intermediate 4: 2-(4-fluorophenyl)pyridin-4-amin

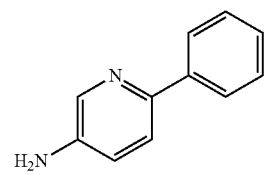 [SMILES: Nc1ccc(-c2ccccc2)nc1]

$^1$H-NMR (400 MHz, DMSO-$d_6$): δ=8.07 (d, 1H), 7.95 (dd, 2H), 7.25 (t, 2H), 6.96 (d, 1H), 6.44 (dd, 1H), 6.06 (s, 2H).

HPLC-MS: Rt 3.328; m/z 189.1 (MH$^+$).

Intermediate 5: 6-phenylpyridin-3-amine

¹H-NMR (400 MHz, DMSO-d₆): δ=8.02 (d, 1H), 7.91 (d, 2H), 7.62 (d, 1H), 7.38 (t, 2H), 7.26 (t, 1H), 6.99 (dd, 1H), 5.45 (s, 2H).
HPLC-MS: Rt 3.442; m/z 170.9 (MH⁺).

Intermediate 6: 6-(4-fluorophenyl)pyridin-3-amine

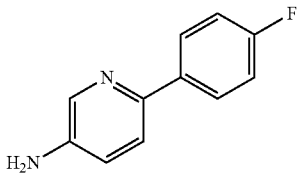 [SMILES: Nc1ccc(-c2ccc(F)cc2)nc1]

¹H-NMR (400 MHz, DMSO-d₆): δ=8.01 (d, 1H), 7.93 (dd, 2H), 7.60 (d, 1H), 7.20 (t, 2H), 6.99 (dd, 1H), 5.45 (s, 2H).
HPLC-MS: Rt 3.670; m/z 188.9 (MH⁺).

Intermediate 7: [2,4'-bipyridin]-4-amine

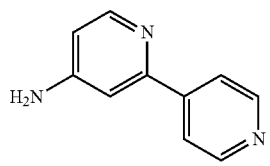 [SMILES: Nc1ccnc(-c2ccncc2)c1]

¹H-NMR (400 MHz, DMSO-d₆): δ=8.64 (d, 2H), 8.13 (d, 1H), 7.86 (d, 2H), 7.11 (d, 1H), 6.54 (dd, 1H), 6.21 (s, 2H).
HPLC-MS: Rt 2.326; m/z 172.0 (MH⁺).

Intermediate 8: [2,4'-bipyridin]-5-amine

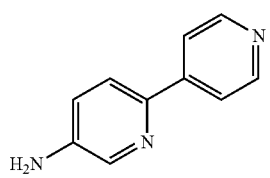 [SMILES: Nc1ccc(-c2ccncc2)nc1]

¹H-NMR (400 MHz, DMSO-d₆): δ=8.54 (d, 2H), 8.07 (d, 1H), 7.87 (d, 2H), 7.79 (d, 1H), 7.01 (dd, 1H), 5.76 (s, 2H).
HPLC-MS: Rt 2.479; m/z 171.9 (MH⁺).

Intermediate 9: [2,3'-bipyridin]-4-amine

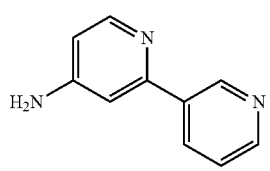 [SMILES: Nc1ccnc(-c2cccnc2)c1]

¹H-NMR (400 MHz, DMSO-d₆): =9.02 (d, 1H), 8.69 (dd, 1H), 8.23 (d, 1H), 8.15 (d, 1H), 7.57 (dd, 2H), 7.28 (s, 1H), 7.08 (d, 1H), 6.70 (dd, 1H).
HPLC-MS: Rt 2.303; m/z 172.0 (MH⁺).

Intermediate 10: [2,3'-bipyridin]-5-amine

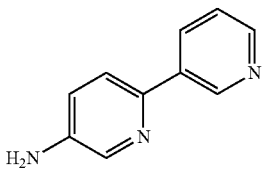 [SMILES: Nc1ccc(-c2cccnc2)nc1]

¹H-NMR (400 MHz, DMSO-d₆): δ=9.10 (d, 1H), 8.46 (dd, 1H), 8.24 (m, 1H), 8.05 (d, 1H), 7.71 (d, 1H), 7.40 (dd, 1H), 7.01 (dd, 1H), 5.58 (s, 2H).
HPLC-MS: Rt 2.471; m/z 172.0 (MH⁺).

Intermediate 11: tert-butyl 3-(5-aminopyridin-2-yl)benzoate

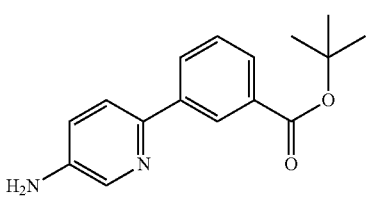 [SMILES: CC(C)(C)OC(=O)c1cccc(-c2ccc(N)cn2)c1]

¹H-NMR (400 MHz, DMSO-d₆): δ=8.45 (s, 1H), 8.12 (d, 1H), 8.05 (d, 1H), 7.79 (d, 1H), 7.67 (d, 1H), 7.50 (t, 1H), 7.02 (dd, 1H), 5.55 (s, 2H), 1.57 (s, 9H).
HPLC-MS: Rt 4.808; m/z 271.1 (MH⁺)

Intermediate 12: methyl 3-(5-aminopyridin-2-yl)benzoate

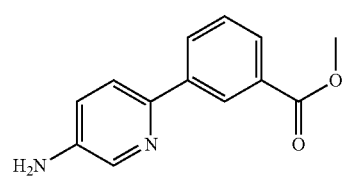 [SMILES: COC(=O)c1cccc(-c2ccc(N)cn2)c1]

¹H-NMR (400 MHz, DMSO-d₆): =8.55 (s, 1H), 8.16 (d, 1H), 8.05 (d, 1H), 7.85 (d, 1H), 7.70 (d, 1H), 7.54 (t, 1H), 7.01 (dd, 1H), 5.56 (s, 2H), 3.88 (s, 3H).
HPLC-MS: Rt 3.731; m/z 229.1 (MH⁺)

Intermediate 13: tert-butyl 4-(5-aminopyridin-2-yl)benzoate

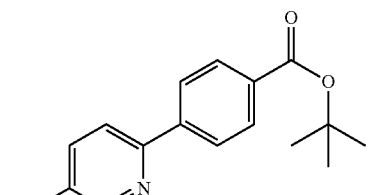

¹H-NMR (400 MHz, DMSO-d₆): δ=8.04 (d, 3H), 7.90 (d, 2H), 7.73 (d, 1H), 7.00 (dd, 1H), 5.66 (s, 2H), 1.55 (s, 9H). HPLC-MS: Rt 4.589; m/z 271.1 (MH⁺)

Intermediate 14: methyl 4-(5-aminopyridin-2-yl)benzoate

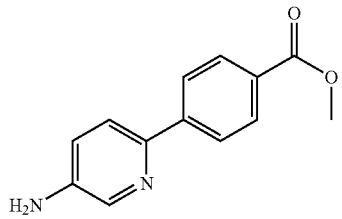 [SMILES: COC(=O)c1ccc(-c2ccc(N)cn2)cc1]

¹H-NMR (400 MHz, DMSO-d₆): δ=8.07 (d, 3H), 7.97 (d, 2H), 7.74 (d, 1H), 7.01 (dd, 1H), 5.66 (s, 2H), 3.85 (s, 3H). HPLC-MS: Rt 3.724; m/z 229.1 (MH⁺)

Intermediate 15: 2-morpholinopyridin-4-amine

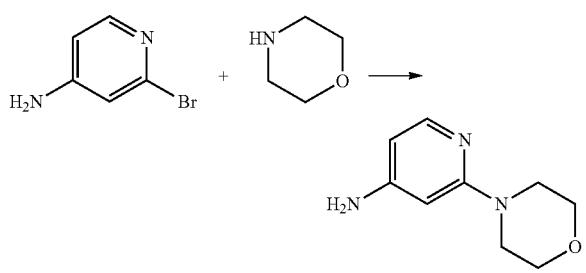

In a sealed flask were solved 2-bromopyridin-4-amine (100 mg, 0.58 mmol) and morpholine (0.25 mL, 2.9 mmol) in 0.8 mL of dry DMSO. Potassium carbonate (239.6 mg, 1.73 mmol) was added to the mixture and the reaction was stirred at 190° C. for 16 hours. The mixture was quenched with NaHCO₃ saturated and extracted with ethyl acetate. The organic layer was dried and concentrated. The crude was purified by CombiFlash column chromatography (DCM/MeOH) to afford the desired product (25 mg, 24.1%).

¹H-NMR (400 MHz, DMSO-d₆): δ=7.63 (d, 1H), 5.98 (dd, 1H), 5.85 (s, 3H), 3.66 (m, 4H), 3.27 (m, 4H). HPLC-MS: Rt 1.661; m/z 180.0 (MH⁺).

The following intermediate was synthesized using the procedure described for the intermediate 15 starting from the corresponding pyridinyl halide and amine.

Intermediate 16: 6-morpholinopyridin-3-amine

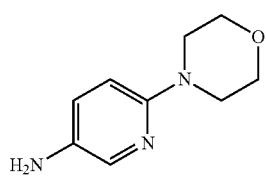

¹H-NMR (400 MHz, DMSO-de): δ=7.61 (s, 1H), 6.93 (d, 1H), 6.62 (d, 1H), 4.66 (s, 2H), 3.68 (s, 4H), 3.17 (s, 4H). HPLC-MS: Rt 1.730; m/z 179.9 (MH⁺).

Intermediate 17: 2-(4-methylpiperazin-1-yl)pyridin-4-amine

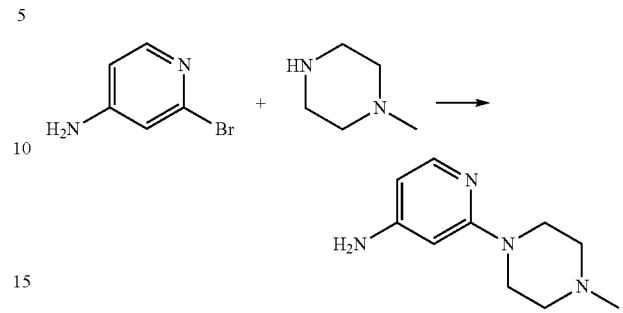

2-bromopyridin-4-amine (100 mg, 0.58 mmol) in 1-metil-piperazine (0.64 mL, 5.8 mmol) were heated in a sealed vial at 135° C. for 16 hours. The reaction was solved in a mixture of diethyl ether and methanol and concentrated. Purification of the solid was carried out by CombiFlash chromatography column (DCM/MeOH) obtained 2-(4-methylpiperazin-1-yl)pyridin-4-amine (84.2 mg, 75.7%).

¹H-NMR (400 MHz, DMSO-de): δ=7.61 (d, 1H), 5.95 (dd, 1H), 5.86 (s, 1H), 5.82 (s, 2H), 3.33 (m, 4H), 3.04 (m, 4H), 2.23 (s, 3H).

HPLC-MS: Rt 1.995; m/z 193.0 (MH⁺).

The following intermediate was synthesized using the procedure described for the intermediate 17 starting from the corresponding pyridinyl halide and amine.

Intermediate 18: 6-(4-methylpiperazin-1-yl)pyridin-3-amine

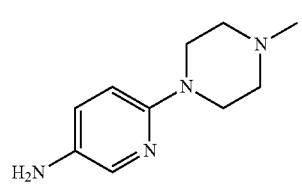

¹H-NMR (400 MHz, DMSO-de): δ=7.59 (s, 1H), 6.90 (d, 1H), 6.62 (d, 1H), 4.61 (s, 2H), 3.23 (s. 4H), 2.46 (s. 4H), 2.25 (s. 3H).

HPLC-MS: Rt 1.903; m/z 192.9 (MH⁺).

Intermediate 19: 2-bromo-5-(2,5-dimethyl-1H-pyrrol-1-yl)pyridine

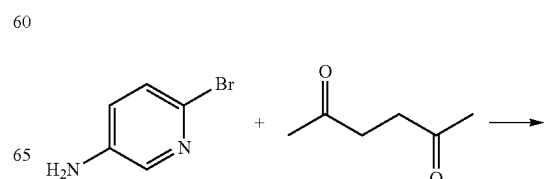

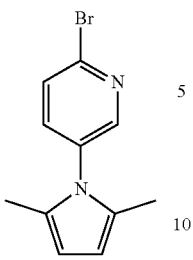

In a settled tube with molecular sieves, were added 6-bromopyridin-3-amine (100 mg, 0.58 mmol), hexane-2,5-dione (0.075 mL, 0.64 mmol) and p-toluensulphonic acid (1.5 mg, 0.008 mmol) in 2 mL of anhydride Toluene. The mixture was stirred for 4 hours at reflux. The reaction mixture was quenched with NaHCO$_3$ saturated and extracted with toluene (×2). The organic layer was dried, concentrated under vacuum and was purified by CombiFlash chromatography column (cyclohexane/ethyl acetate) to obtain the desired intermediate (83.2 mg, 57.3%).

$^1$H-NMR (400 MHz, DMSO-d$_6$): δ=8.39 (d, 1H), 7.79 (m, 2H), 5.85 (s, 2H), 1.99 (s, 6H).

HPLC-MS: Rt 4.958; m/z 251.8 (MH$^+$).

The following intermediate was synthesized using the procedure described for the intermediate 19 starting from the corresponding amine.

Intermediate 20:
2-bromo-4-(2,5-dimethyl-1H-pyrrol-1-yl)pyridine

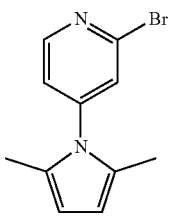

$^1$H-NMR (400 MHz, DMSO-d$_6$): δ=8.51 (d, 1H), 7.72 (s, 1H), 7.45 (d, 1H), 5.88 (s, 2H), 2.06 (s, 6H).

HPLC-MS: Rt 4.892; m/z 251.8 (MH$^+$).

Intermediate 21: 5-(2,5-dimethyl-1H-pyrrol-1-yl)-2,2'-bipyridine

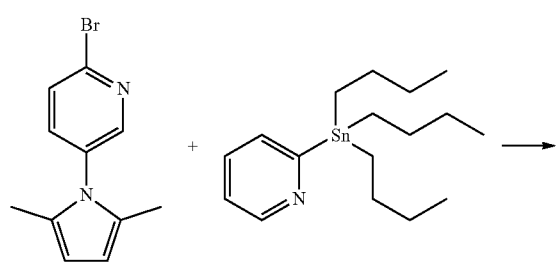

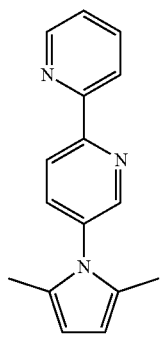

To a solution of 2-bromo-5-(2,5-dimethyl-1H-pyrrol-1-yl)pyridine (73.2 mg, 0.29 mmol) in 1.5 mL of dry toluene at room temperature, was added 2-(tributylstannyl)pyridine (0.02 mL, 0.44 mmol) dropwise under N$_2$ atmosphere following by the addition of tetrakis(triphenylphosphine)palladium (10.1 mg, 0.009 mmol). The reaction mixture was degassed with nitrogen and was stirred at 130° C. overnight. The reaction was cooled to room temperature. Next, the mixture was taken up with NaOH 2M and separated with ethyl acetate (×2). The organic layer was washed with brine, was dried with Na$_2$SO$_4$ and the solvent was removed under vacuum. The crude was purified by CombiFlash chromatography column (cyclohexane/ethyl acetate) to afford the desired compound (60.2 mg, 82.9%).

$^1$H-NMR (400 MHz, DMSO-d$_6$): δ=8.77 (d, 1H), 8.68 (d, 1H), 8.55 (d, 1H), 8.51 (d, 1H), 8.12 (t, 1H), 7.98 (dd, 1H), 7.60 (m, 1H), 5.89 (s, 2H), 2.04 (s, 6H).

HPLC-MS: Rt 5.044; m/z 249.9 (MH$^+$).

The following intermediate was synthesized using the procedure described for the intermediate 21 starting from the corresponding (2,5-dimethyl-1H-pyrrol-1-yl)pyridine derivative.

Intermediate 22: 4-(2,5-dimethyl-1H-pyrrol-1-yl)-2,2'-bipyridine

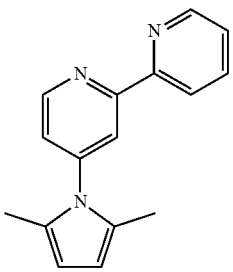 [SMILES: Cc1ccc(C)n1-c1ccnc(-c2ccccn2)c1]

$^1$H-NMR (400 MHz, DMSO-d$_6$): δ=8.82 (d, 1H), 8.70 (d, 1H), 8.45 (d, 1H), 8.19 (d, 1H), 8.00 (t, 1H), 7.48 (m, 2H), 5.91 (s, 2H), 2.08 (s, 6H).

HPLC-MS: Rt 5.056; m/z 249.9 (MH$^+$).

Intermediate 23: [2,2'-bipyridin]-5-amine

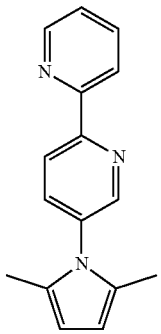   +   NH$_2$OH·HCl   +   Et$_3$N   →   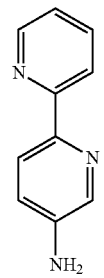

Method A: The mixture of 5-(2,5-dimethyl-1H-pyrrol-1-yl)-2,2'-bipyridine (75.6 mg, 0.3 mmol), hydroxylamine hydrochloride (210.7 mg, 3.0 mmol) and triethylamine (0.084 mL, 0.6 mmol) in 1.4 mL ethanol and 0.6 mL of H$_2$O was stirred at 80° C. for 20 hours. The mixture was poured over HCl 1M and was washed with diethyl ether. The aqueous layer was neutralized and basified with NaOH 5M and NaOH 2M until obtained pH=9-10 and was extracted with dichloromethane (×3). The different organic layers were collected and were dried. The crude was purified by CombiFlash chromatography column (dichloromethane/dichloromethane:methanol 20%) to afforded the amine derivative (19.6 mg, 37.8%).

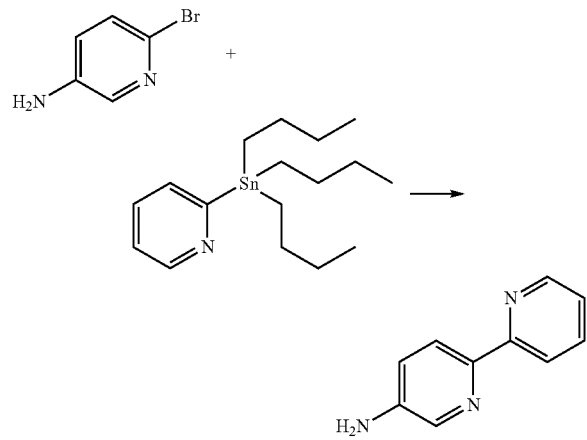

Method B: To a solution of 6-bromopyridin-3-amine (50 mg, 0.29 mmol) in 1.5 mL of dry toluene at room temperature, was added 2-(tributylstannyl)pyridine (0.013 mL, 0.35 mmol) dropwise under N$_2$ atmosphere following by the addition of tetrakis(triphenylphosphine)palladium (40.2 mg, 0.03 mmol). The reaction mixture was degassed with nitrogen and was stirred at 130° C. for two days. The reaction was cooled to room temperature. Next, the mixture was taken up with NaOH 2M and separated with ethyl acetate (×2). The organic layer was washed with brine, was dried with Na$_2$SO$_4$ and the solvent was removed under vacuum. The crude was purified by CombiFlash chromatography column (DCM/DCM:MeOH 20%) to afforded the desired compound (21.6 mg, 43.5%).

$^1$H-NMR (400 MHz, DMSO-d$_6$): δ=8.54 (d, 1H), 8.17 (d, 1H), 8.08 (d, 1H), 8.01 (d, 1H), 7.80 (td, 1H), 7.25 (m, 1H), 7.01 (dd, 1H), 5.65 (s, 2H).

HPLC-MS: Rt 2.746; m/z 172.0 (MH$^+$).

The following intermediate was synthesized using the procedure described for the intermediate 23 starting from the corresponding derivatives.

Intermediate 24: [2,2'-bipyridin]-4-amine

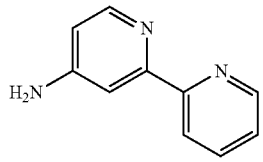 [SMILES: Nc1ccnc(-c2ccccn2)c1]

$^1$H-NMR (400 MHz, DMSO-d$_6$): δ=8.62 (d, 1H), 8.29 (d, 1H), 8.09 (d, 1H), 7.88 (td, 1H), 7.61 (d, 1H), 7.39 (dd, 1H), 6.53 (dd, 1H), 6.27 (s, 2H).

HPLC-MS: Rt 2.851; m/z 171.9 (MH$^+$).

Intermediate 25: 6-cyclopropylpyridin-3-amine

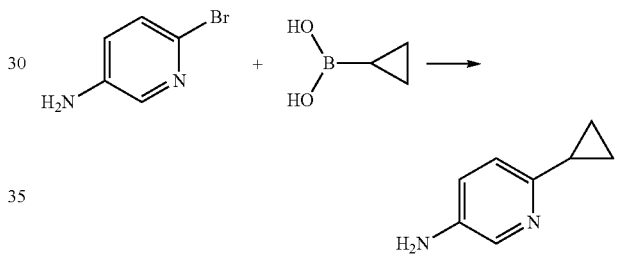

In a sealed tube were mixed 300 mg (1.73 mmol) of 6-bromopyridin-3-amine, 297.9 mg (3.47 mmol) of cyclopropylboronic acid, 97.25 mg (0.35 mmol) of tricyclohexylphosphine, 38.92 mg (0.17 mmol) of Palladium acetate and 1104 mg (5.20 mmol) of potassium phosphate in 12 mL of toluene and 0.6 mL of H$_2$O. The reaction mixture was degassed with N$_2$ and was stirred at 100° C. for two days. The mixture was taken up with ethyl acetate and was extracted with NaOH 1M (×2). The organic layer was dried under vacuum and the crude was purified by chromatography column (Combi-Flash hexane:ethyl acetate) to obtain 28 mg (0.21 mmol, 12.03%) of 6-cyclopropylpyridin-3-amine.

$^1$H-NMR (400 MHz, DMSO-d$_6$): δ=7.77 (d, 1H), 6.89 (d, 1H), 6.81 (dd, 1H), 4.96 (s, 2H), 1.85 (m, 1H), 0.75 (m, 2H), 0.70 (m, 2H).

HPLC-MS: Rt 2.589; m/z 135.1 (MH$^+$)

Intermediate 26: N-(2-bromopyridin-4-yl)-2-chloro-5-cyanobenzamide

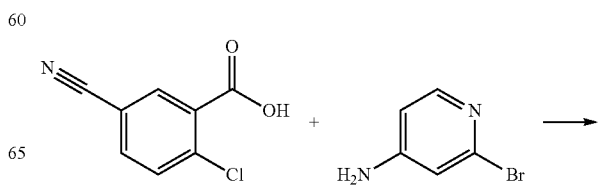

-continued

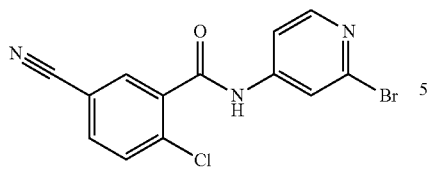

The mixture of 2-chloro-5-cyanobenzoic acid (50 mg, 0.27 mmol), 2-bromopyridin-4-amine (47.6 mg, 0.27 mmol) and EDC (116.2 mg, 0.60 mmol) in 0.5 mL of pyridine was stirred at 60° for 48 hours. The pyridine was removed under vacuum and the resulting crude was purified by CombiFlash chromatography column (Hexane/ethyl acetate) to obtain the desired product (6.2 mg, 6.7%).

$^1$H-NMR (400 MHz, DMSO-d$_6$): δ=11.23 (s, 1H), 8.33 (d, 1H), 8.27 (d, 1H), 8.05 (dd, 1H), 7.98 (s, 1H), 7.86 (d, 1H), 7.60 (dd, 1H).

HPLC-MS: Rt 4.289; m/z 337.9 (MH$^+$).

The following intermediates were synthesized using the procedure described for the intermediate 26 starting from the corresponding derivatives.

Intermediate 27:
N-(6-bromopyridin-3-yl)-2-chloro-5-cyanobenzamide

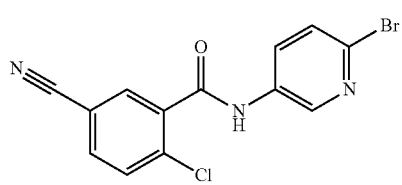 [SMILES: N#Cc1ccc(Cl)c(C(=O)Nc2ccc(Br)nc2)c1]

$^1$H-NMR (400 MHz, DMSO-d$_6$): δ=11.01 (s, 1H), 8.68 (s, 1H), 8.25 (d, 1H), 8.09 (dd, 1H), 8.03 (dd, 1H), 7.85 (d, 1H), 7.68 (d, 1H).

HPLC-MS: Rt 4.243; m/z 337.9 (MH$^+$).

Intermediate 28: tert-butyl 3-(5-(2-chloro-5-cyano-benzamido)pyridin-2-yl)benzoate

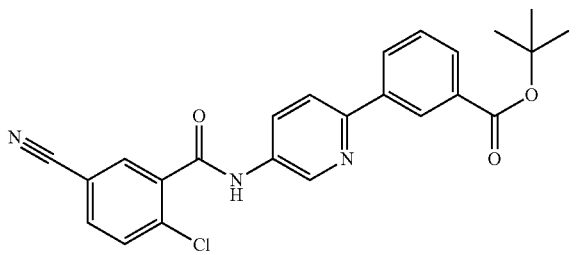 [SMILES: CC(C)(C)OC(=O)c1cccc(-c2ccc(NC(=O)c3cc(C#N)ccc3Cl)cn2)c1]

$^1$H-NMR (400 MHz, DMSO-d$_6$): δ=11.01 (s, 1H), 8.94 (d, 1H), 8.59 (s, 1H), 8.30 (m, 3H), 8.08 (d, 1H), 8.04 (dd, 1H), 7.94 (d, 1H), 7.86 (d, 1H), 7.62 (t, 1H), 1.59 (s, 9H).

HPLC-MS: Rt 5.584; m/z 434.1 (MH$^+$)

Intermediate 29: tert-butyl 4-(5-(2-chloro-5-cyano-benzamido)pyridin-2-yl)benzoate

$^1$H-NMR (400 MHz, DMSO-d$_6$): δ=11.05 (s, 1H), 8.95 (d, 1H), 8.30 (m, 2H), 8.20 (d, 2H), 8.11 (d, 1H), 8.04 (dd, 1H), 8.00 (d, 2H), 7.86 (d, 1H), 1.57 (s, 9H).

HPLC-MS: Rt 5.610; m/z 434.1 (MH$^+$)

Intermediate 30: pyridazin-4-ylamine

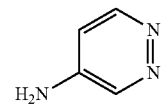

This product is commercially available and can also be obtained as described in Hara, H. and Van Der Plas, H. C. (1982), On the amination of azaheterocycles. A new procedure for the introduction of an amino group. Journal of Heterocyclic Chemistry, 19: 1285-1287. doi:10.1002/jhet.5570190605.

Final Products

Example 1:
2-chloro-5-cyano-N-(2-phenylpyridin-4-yl)benzamide

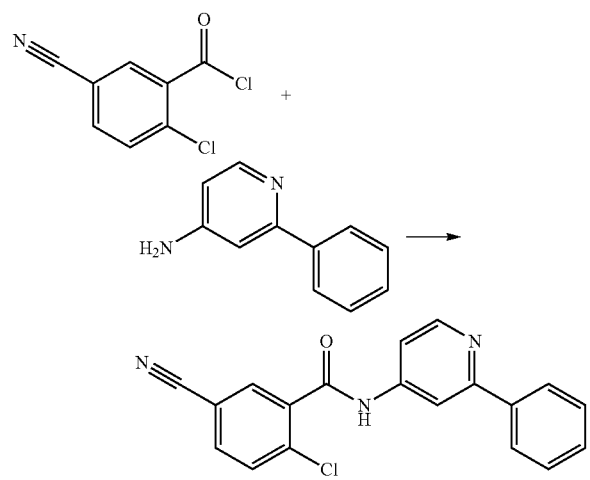

2-chloro-5-cyanobenzoyl chloride (intermediate 1) (55.1 mg, 0.27 mmol) in dry DCM was added dropwise in a cooling mixture of 2-phenylpyridin-4-amine (intermediate 3) (42.5 mg, 0.25 mmol), triethylamine (0.05 mL, 0.37 mmol) in 1 mL of dry DCM. The reaction mixture was stirred at 40° C. overnight. The mixture was extracted with DCM and NaHCO₃ saturated. The organic layer was dried (Na₂SO₄) and concentrated. The crude was purified by CombiFlash column chromatography (Cyclohexane/ethyl acetate) to afford the amide derivative (54.2, 59.1%).

¹H-NMR (400 MHz, DMSO-d₆): δ=11.11 (s, 1H), 8.61 (d, 1H), 8.29 (d, 1H), 8.20 (s, 1H), 8.05 (dd, 1H), 7.99 (d, 2H), 7.86 (d, 1H), 7.64 (d, 1H), 7.52 (t, 2H), 7.46 (t, 1H).

HPLC-MS: Rt 4.737; m/z 333.8 (MH⁺).

The following examples were synthesized using the procedure described for example 1 starting from the corresponding substituted benzoic acid chlorides and amines.

Example 2: 2-chloro-5-cyano-N-(6-phenylpyridin-3-yl)benzamide (Using Intermediates 1 and 5)

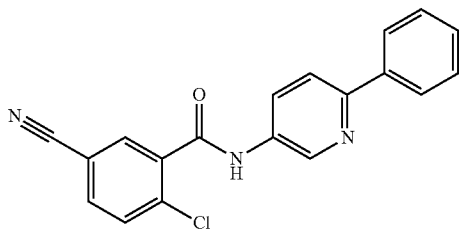

¹H-NMR (400 MHz, DMSO-d₆): δ=10.96 (s, 1H), 8.91 (d, 1H), 8.27 (t, 1H), 8.24 (d, 1H), 8.04 (m, 4H), 7.85 (d, 1H), 7.49 (t, 2H), 7.42 (t, 1H).

HPLC-MS: Rt 4.785; m/z 333.8 (MH⁺).

Example 3: 2-chloro-5-cyano-N-(2-(4-fluorophenyl)pyridin-4-yl)benzamide

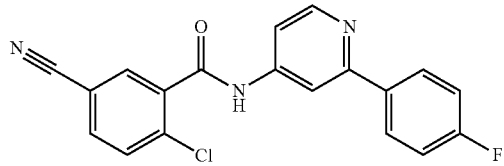 [SMILES: N#Cc1ccc(Cl)c(C(=O)Nc2ccnc(-c3ccc(F)cc3)c2)c1]

¹H-NMR (400 MHz, DMSO-d₆): δ=11.11 (s, 1H), 8.60 (d, 1H), 8.28 (s, 1H), 8.19 (s, 1H), 8.04 (t, 3H), 7.86 (d, 1H), 7.62 (d, 1H), 7.35 (t, 2H).

HPLC-MS: Rt 4.838; m/z 351.8 (MH⁺).

Example 4: 2-chloro-5-cyano-N-(6-(4-fluorophenyl)pyridin-3-yl)benzamide (Using Intermediates 1 and 6)

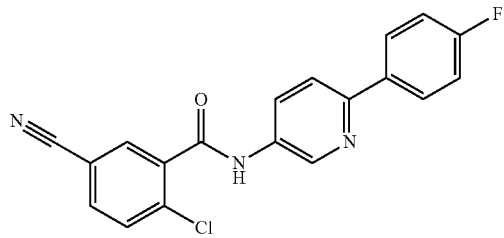 [SMILES: N#Cc1ccc(Cl)c(C(=O)Nc2ccc(-c3ccc(F)cc3)nc2)c1]

¹H-NMR (400 MHz, DMSO-d₆): δ=10.96 (s, 1H), 8.90 (s, 1H), 8.25 (d, 2H), 8.12 (m, 2H), 8.02 (t, 2H), 7.85 (d, 1H), 7.31 (t, 2H).

HPLC-MS: Rt 4.870; m/z 351.8 (MH⁺).

Example 5: N-([2,3'-bipyridin]-5-yl)-2-chloro-5-cyanobenzamide (Using Intermediates 1 and 10)

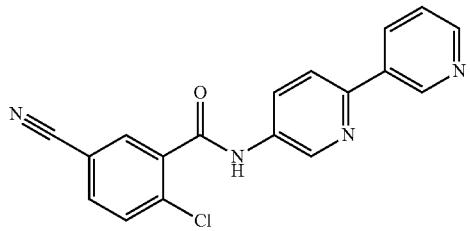 [SMILES: N#Cc1ccc(Cl)c(C(=O)Nc2ccc(-c3cccnc3)nc2)c1]

¹H-NMR (400 MHz, DMSO-d₆): δ=11.02 (s, 1H), 9.25 (d, 1H), 8.95 (d, 1H), 8.62 (dd, 1H), 8.42 (d, 1H), 8.29 (dd, 2H), 8.11 (d, 1H), 8.04 (dd, 1H), 7.86 (d, 1H), 7.52 (dd, 1H).

HPLC-MS: Rt 3.897; m/z 334.8 (MH⁺).

Example 6: N-([2,3'-bipyridin]-4-yl)-2-chloro-5-cyanobenzamide (Using Intermediates 1 and 9)

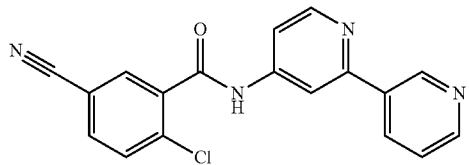 [SMILES: N#Cc1ccc(Cl)c(C(=O)Nc2ccnc(-c3cccnc3)c2)c1]

¹H-NMR (400 MHz, DMSO-d₆): =11.17 (s, 1H), 9.16 (d, 1H), 8.66 (d, 2H), 8.33 (d, 1H), 8.28 (d, 1H), 8.22 (s, 1H), 8.05 (dd, 1H), 7.87 (d, 1H), 7.71 (d, 1H), 7.55 (dd, 1H).

HPLC-MS: Rt 3.908; m/z 334.8 (MH⁺).

Example 7: N-([2,4'-bipyridin]-5-yl)-2-chloro-5-cyanobenzamide

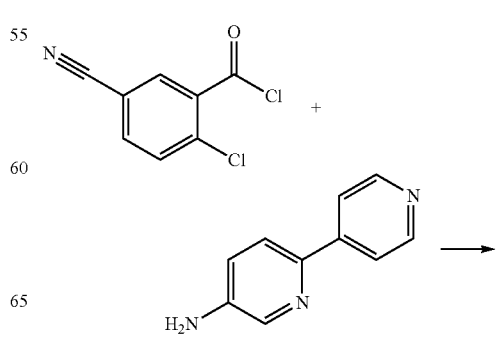

-continued

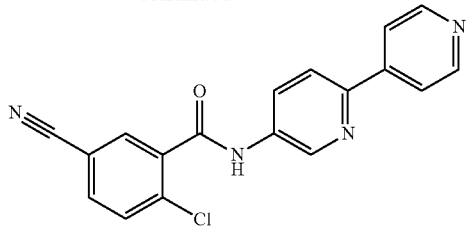

2-chloro-5-cyanobenzoyl chloride (intermediate 1) (64.3 mg, 0.32 mmol) in dry acetonitrile was added dropwise in a solution of [2,4'-bipyridin]-5-amine (intermediate 8) (50 mg, 0.29 mmol), triethylamine (0.05 mL, 0.37 mmol) and 4-DMAP (0.36 mg, 0.0029 mmol) in 3 mL of dry acetonitrile. The reaction mixture was stirred at 50° C. overnight. The mixture was quenched with water and was extracted three times with ethyl acetate. The organic layer was dried ($Na_2SO_4$) and concentrated. The crude was purified by CombiFlash column chromatography (DCM/Methanol) to afford the amide derivative (21.7, 22.2%).

$^1$H-NMR (400 MHz, DMSO-$d_6$): δ=11.09 (s, 1H), 8.97 (d, 1H), 8.69 (d, 2H), 8.33 (dd, 1H), 8.29 (d, 1H), 8.19 (d, 1H), 8.05 (dd, 3H), 7.86 (d, 1H).

HPLC-MS: Rt 3.874; m/z 334.8 (MH$^+$).

The following examples were synthesized using the procedure described for the example 7 starting from the corresponding substituted benzoic acid chlorides and amines.

Example 8: N-([2,4'-bipyridin]-4-yl)-2-chloro-5-cyanobenzamide (Using Intermediates 1 and 7)

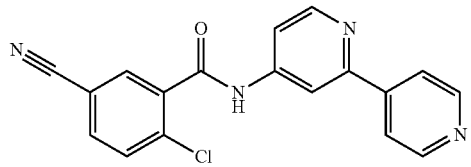 [SMILES: N#Cc1ccc(Cl)c(C(=O)Nc2ccnc(-c3ccncc3)c2)c1]

$^1$H-NMR (400 MHz, DMSO-$d_6$): δ=11.21 (s, 1H), 8.70 (m, 3H), 8.30 (d, 2H), 8.06 (d, 1H), 7.94 (s, 2H), 7.87 (d, 1H), 7.75 (s, 1H).

HPLC-MS: Rt 3.902; m/z 334.8 (MH$^+$).

Example 9: N-([2,3'-bipyridin]-5-yl)-5-cyano-2-fluorobenzamide (Using Intermediates 2 and 10)

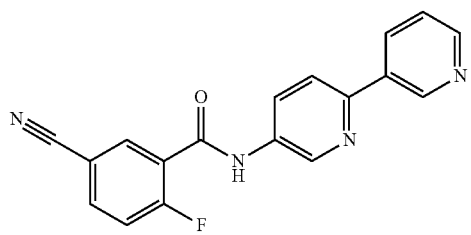 [SMILES: N#Cc1ccc(F)c(C(=O)Nc2ccc(-c3cccnc3)nc2)c1]

$^1$H-NMR (400 MHz, DMSO-$d_6$): δ=10.96 (s, 1H), 9.25 (d, 1H), 8.97 (d, 1H), 8.61 (d, 1H), 8.42 (d, 1H), 8.30 (m, 2H), 8.13 (dd, 2H), 7.66 (t, 1H), 7.52 (dd, 1H).

HPLC-MS: Rt 3.759; m/z 318.8 (MH$^+$).

Example 10: 5-cyano-2-fluoro-N-(6-(4-fluorophenyl)pyridin-3-yl)benzamide (Using Intermediates 2 and 6)

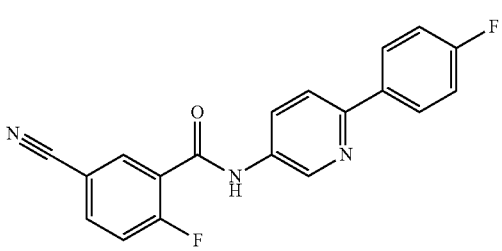 [SMILES: N#Cc1ccc(F)c(C(=O)Nc2ccc(-c3ccc(F)cc3)nc2)c1]

$^1$H-NMR (400 MHz, DMSO-$d_6$): δ=10.90 (s, 1H), 8.92 (d, 1H), 8.31 (dd, 1H), 8.24 (dd, 1H), 8.14 (td, 3H), 8.01 (d, 1H), 7.66 (t, 1H), 7.31 (t, 2H).

HPLC-MS: Rt 4.816; m/z 335.8 (MH$^+$).

Example 11: 5-cyano-2-fluoro-N-(2-(4-fluorophenyl)pyridin-4-yl)benzamide (Using Intermediates 2 and 4)

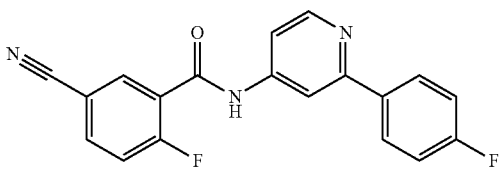 [SMILES: N#Cc1ccc(F)c(C(=O)Nc2ccnc(-c3ccc(F)cc3)c2)c1]

$^1$H-NMR (400 MHz, DMSO-$d_6$): δ=11.04 (s, 1H), 8.60 (d, 1H), 8.31 (dd, 1H), 8.19 (d, 1H), 8.16 (dd, 1H), 8.04 (dd, 2H), 7.68 (d, 1H), 7.64 (m, 1H), 7.35 (t, 2H).

HPLC-MS: Rt 4.724; m/z 335.8 (MH$^+$).

Example 12: N-([2,3'-bipyridin]-4-yl)-5-cyano-2-fluorobenzamide (Using Intermediates 2 and 9)

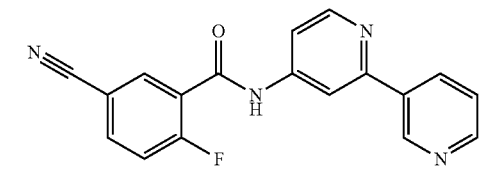 [SMILES: N#Cc1ccc(F)c(C(=O)Nc2ccnc(-c3cccnc3)c2)c1]

$^1$H-NMR (400 MHz, DMSO-$d_6$): δ=11.10 (s, 1H), 9.16 (d, 1H), 8.66 (d, 2H), 8.32 (t, 2H), 8.24 (d, 1H), 8.16 (m, 1H), 7.72 (dd, 1H), 7.67 (t, 1H), 7.55 (dd, 1H).

HPLC-MS: Rt 3.756; m/z 318.9 (MH$^+$).

Example 13: N-([2,2'-bipyridin]-5-yl)-2-chloro-5-cyanobenzamide (Using Intermediates 1 and 23)

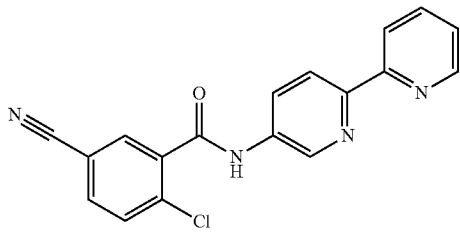

$^1$H-NMR (400 MHz, DMSO-d$_6$): δ=11.04 (s, 1H), 8.93 (d, 1H), 8.67 (d, 1H), 8.43 (d, 1H), 8.35 (d, 2H), 8.30 (dd, 1H), 8.04 (dd, 1H), 7.94 (td, 1H), 7.86 (d, 1H), 7.43 (dd, 1H).

HPLC-MS: Rt 4.229; m/z 334.8 (MH$^+$).

Example 14: 2-chloro-5-cyano-N-(6-(4-methylpiperazin-1-yl)pyridin-3-yl)benzamide (Using Intermediates 1 and 18)

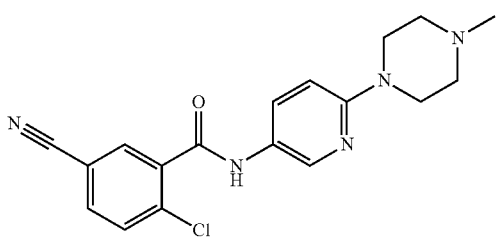 [SMILES: CN1CCN(c2ccc(NC(=O)c3cc(C#N)ccc3Cl)cn2)CC1]

$^1$H-NMR (400 MHz, DMSO-d$_6$): δ=10.47 (s, 1H), 8.38 (d, 1H), 8.18 (d, 1H), 7.99 (dd, 1H), 7.86 (dd, 1H), 7.81 (d, 1H), 6.87 (d, 1H), 3.44 (m, 4H), 2.40 (m, 4H), 2.21 (s, 3H).

HPLC-MS: Rt 3.618; m/z 355.9 (MH$^+$).

Example 15: 2-chloro-5-cyano-N-(2-(4-methylpiperazin-1-yl)pyridin-4-yl)benzamide (Using Intermediates 1 and 17)

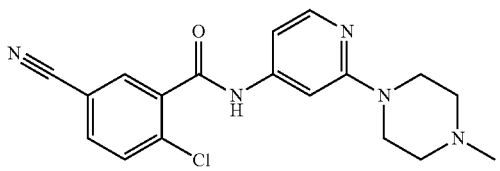 [SMILES: CN1CCN(c2cc(NC(=O)c3cc(C#N)ccc3Cl)ccn2)CC1]

$^1$H-NMR (400 MHz, DMSO-d$_6$): δ=10.74 (s, 1H), 8.20 (d, 1H), 8.04 (d, 1H), 8.01 (dd, 1H), 7.83 (d, 1H), 7.19 (s, 1H), 6.90 (d, 1H), 3.44 (d, 4H), 2.40 (m, 4H), 2.22 (s, 3H).

HPLC-MS: Rt 3.776; m/z 355.8 (MH$^+$).

Example 16: 2-chloro-5-cyano-N-(2-morpholinopyridin-4-yl)benzamide (Using Intermediates 1 and 15)

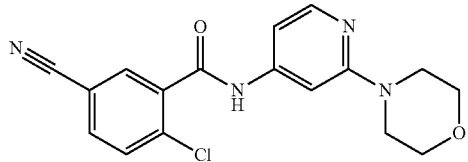 [SMILES: N#Cc1ccc(Cl)c(C(=O)Nc2ccnc(N3CCOCC3)c2)c1]

$^1$H-NMR (400 MHz, DMSO-d$_6$): δ=10.93 (s, 1H), 8.22 (d, 1H), 8.07 (d, 1H), 8.03 (dd, 1H), 7.84 (d, 1H), 7.28 (s, 1H), 6.98 (d, 1H), 3.72 (s, 4H), 3.43 (s, 4H).

HPLC-MS: Rt 3.938; m/z 342.8 (MH$^+$).

Example 17: 2-chloro-5-cyano-N-(6-morpholinopyridin-3-yl)benzamide (Using Intermediates 1 and 16)

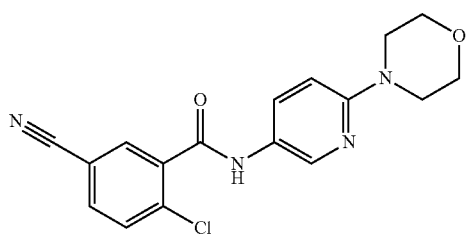 [SMILES: N#Cc1ccc(Cl)c(C(=O)Nc2ccc(N3CCOCC3)nc2)c1]

$^1$H-NMR (400 MHz, DMSO-d$_6$): δ=10.50 (s, 1H), 8.41 (d, 1H), 8.19 (d, 1H), 7.99 (dd, 1H), 7.90 (dd, 1H), 7.81 (d, 1H), 6.88 (d, 1H), 3.70 (m, 4H), 3.40 (m, 4H).

HPLC-MS: Rt 3.774; m/z 342.8 (MH$^+$).

Example 18: N-([2,4'-bipyridin]-4-yl)-5-cyano-2-fluorobenzamide (Using Intermediates 2 and 7)

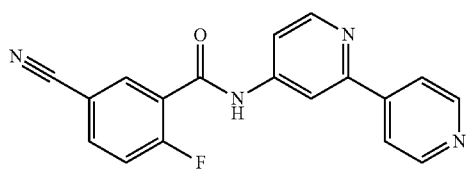 [SMILES: N#Cc1ccc(F)c(C(=O)Nc2ccnc(-c3ccncc3)c2)c1]

H$^1$-RMN (400 MHz, DMSO-d$_6$): 11.14 (s, 1H), 8.71 (dd, 3H), 8.33 (s, 2H), 8.18 (d, 1H), 7.95 (d, 2H), 7.76 (d, 1H), 7.67 (t, 1H).

HPLC-MS: 3.811; m/z 319.0 (MH$^+$)

Example 19: N-([2,4'-bipyridin]-5-yl)-5-cyano-2-fluorobenzamide (Using Intermediates 2 and 8)

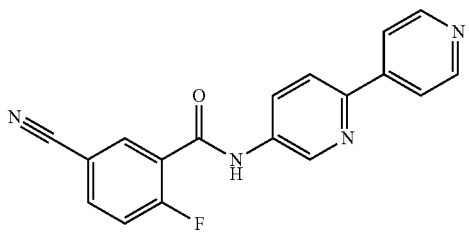 [SMILES: N#Cc1ccc(F)c(C(=O)Nc2ccc(-c3ccncc3)nc2)c1]

$^1$H-NMR (400 MHz, DMSO-d$_6$): δ=11.02 (s, 1H), 8.99 (s, 1H), 8.69 (d, 2H), 8.33 (dd, 2H), 8.19 (d, 1H), 8.15 (m, 1H), 8.04 (d, 2H), 7.66 (t, 1H).

HPLC-MS: Rt 3.829; m/z 319.0 (MH$^+$).

Example 20: 2-chloro-5-cyano-N-(pyridazin-4-yl)benzamide (Using Intermediates 1 and 30)

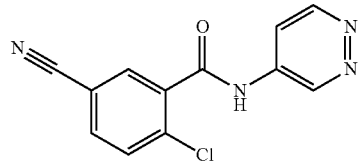 [SMILES: N#Cc1ccc(Cl)c(C(=O)Nc2ccnnc2)c1]

$^1$H-NMR (400 MHz, DMSO-d$_6$): δ=11.31 (s, 1H), 9.36 (d, 1H), 9.13 (d, 1H), 8.30 (d, 1H), 8.06 (dd, 1H), 8.03 (dd, 1H), 7.87 (d, 1H).

HPLC-MS: Rt 3.149; m/z 259.0 (MH$^+$).

Example 21: 5-cyano-2-fluoro-N-(pyridazin-4-yl)benzamide (Using Intermediates 2 and 30)

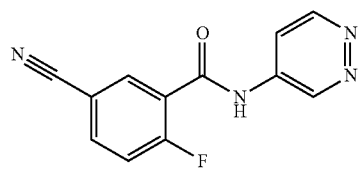 [SMILES: N#Cc1ccc(F)c(C(=O)Nc2ccnnc2)c1]

$^1$H-NMR (400 MHz, DMSO-d$_6$): δ=11.23 (s, 1H), 9.39 (m, 1H), 9.13 (d, 1H), 8.32 (dd, 1H), 8.18 (m, 1H), 8.03 (dd, 1H), 7.67 (m, 1H).

HPLC-MS: Rt 2.958; m/z 243.0 (MH$^+$).

Example 22: 2-chloro-5-cyano-N-(6-cyclopropylpyridin-3-yl)benzamide (Using Intermediates 1 and 25)

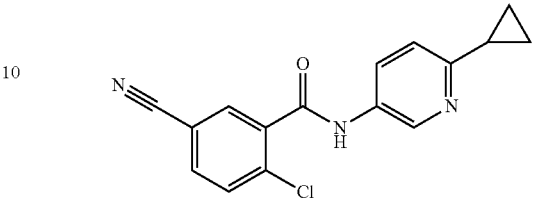

$^1$H-NMR (400 MHz, DMSO-d$_6$): δ=10.73 (s, 1H), 8.63 (d, 1H), 8.21 (d, 1H), 8.00 (m, 2H), 7.82 (d, 1H), 7.30 (d, 1H), 2.08 (m, 1H), 0.92 (m, 2H), 0.88 (m, 2H).

HPLC-MS: Rt 4.239; m/z 296.1 (MH$^+$)

Example 23: 3-(5-(2-chloro-5-cyanobenzamido)pyridin-2-yl)benzoic Acid

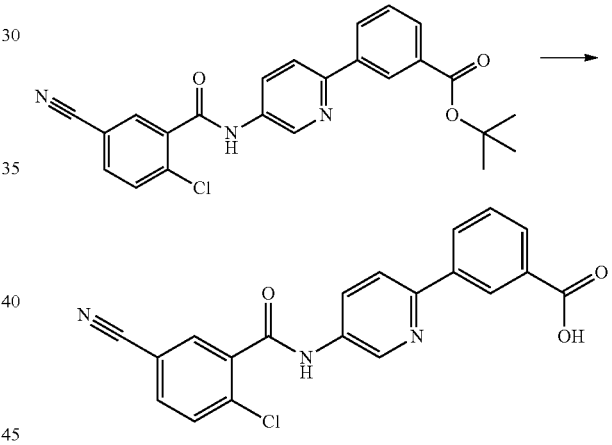

To a solution of 76 mg (0.175 mmol) of tert-butyl 3-(5-(2-chloro-5-cyanobenzamido)pyridin-2-yl)benzoate (intermediate 28) in 2 mL of dry DCM, were added 0.3 mL (3.5 mmol) of trifluoroacetic acid. The reaction was stirred at room temperature for 8 hours. The solvent was remove under reduce pressure. The obtained solid was washed with THF and Methanol and was filtrated. The filtrate was purified by Combi-Flash column chromatography (DCM/MeOH) to afford the desired carboxyl acid derivative (22.3 mg, 33.7%)

$^1$H-NMR (400 MHz, DMSO-d$_6$): δ=13.11 (s, 1H), 11.01 (s, 1H), 8.94 (d, 1H), 8.66 (s, 1H), 8.30 (m, 3H), 8.09 (d, 1H), 8.04 (dd, 1H), 7.98 (d, 1H), 7.86 (d, 1H), 7.62 (t, 1H).

HPLC-MS: Rt 2.991; m/z 378.0 (MH$^+$)

The following example was synthesized using the procedure described for the example 23 starting from the corresponding substituted benzoic acid chlorides and amines.

Example 24: 4-(5-(2-chloro-5-cyanobenzamido)pyridin-2-yl)benzoic acid (Using Intermediate 29)

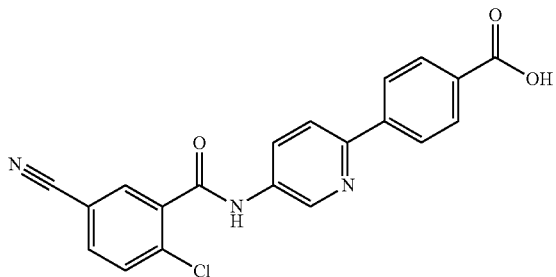 [SMILES: N#Cc1ccc(Cl)c(C(=O)Nc2ccc(-c3ccc(C(=O)O)cc3)nc2)c1]

$^1$H-NMR (400 MHz, DMSO-d$_6$): δ=13.05 (s, 1H), 11.05 (s, 1H), 8.95 (d, 1H), 8.30 (dd, 2H), 8.20 (d, 2H), 8.12 (d, 1H), 8.05 (d, 3H), 7.86 (d, 1H).

HPLC-MS: Rt 2.899; m/z 378.0 (MH$^+$)

The invention claimed is:

1. A compound of formula (I):

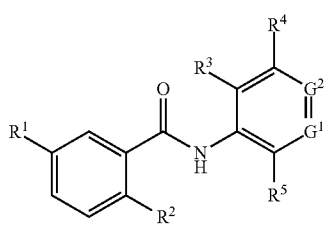

(I)

wherein:
R$^2$ is Cl or F atoms,
R$^1$ represents a cyano group,
G$^1$ and G$^2$ independently represent N atom or —CR$^9$, wherein G$^1$ and G$^2$ are not simultaneously CR$^9$,
R$^9$ is independently selected from the group consisting of:
  a) five or a six-membered heteroaryl ring optionally substituted by one or more substituents selected from the group consisting of halogen atom, cyano group, —COOH group, linear or branched C$_1$-C$_3$ alkyl group, linear or branched C$_1$-C$_3$ alkoxy, linear or branched C$_1$-C$_3$ haloalkyl group, C$_3$-C$_4$ cycloalkyl, and C$_3$-C$_4$ cycloalkoxy,
  b) phenyl group optionally substituted by one or more substituents selected from the group consisting of halogen atom, cyano group, —COOH group, linear or branched C1-C3 alkyl group, linear or branched C1-C3 alkoxy, linear or branched C1-C3 haloalkyl group, C3-C4 cycloalkyl, and C3-C4 cycloalkoxy,
  c) a five or six-membered saturated heterocyclic ring comprising one or two heteroatoms selected from N and O as part of the cycle, which heterocycle is optionally substituted by a C$_1$-C$_3$ alkyl group or C$_3$-C$_4$ cycloalkyl group, and
  d) —C$_3$-C$_6$ cycloalkyl group, and
R$^3$, R$^4$ and R$^5$ are independently selected from the group consisting of hydrogen atom, halogen atom, linear or branched C$_1$-C$_3$ alkyl group, C$_3$-C$_4$ cycloalkyl group and cyano group,
or pharmaceutically acceptable salts thereof.

2. The compound according to claim 1, wherein R$^3$, R$^4$ and R$^5$ are independently selected from the group consisting of hydrogen atom and halogen atom.

3. The compound according to claim 1, wherein R$^3$, R$^4$ and R$^5$ are hydrogen atoms.

4. The compound according to claim 1, wherein G$^1$ represents a N atom and G$^2$ represents a —CR$^9$ group, wherein R$^9$ is selected from the group consisting of:
  a) phenyl group optionally substituted by one or more substituents selected from the group consisting of halogen atom and —COOH group,
  b) a pyridyl ring optionally substituted by one or more substituents selected from the group consisting of halogen atom and cyano group, and
  c) a morpholinyl and piperazinyl group optionally substituted by a C$_1$-C$_3$ alkyl group or C$_3$-C$_6$ cycloalkyl group.

5. The compound according to claim 1 wherein G$^2$ represents a N atom and G$^1$ represents a —CR$^9$ group, wherein R$^9$ is selected from the group consisting of:
  a) phenyl group optionally substituted by one or more substituents selected from the group consisting of halogen atom and —COOH group,
  b) pyridinyl ring optionally substituted by one or more substituents selected from the group consisting of halogen atom and cyano group, and
  c) a morpholinyl and piperazinyl groups optionally substituted by a group selected from of C$_1$-C$_3$ alkyl group and C$_3$-C$_6$ cycloalkyl group.

6. The compound according to claim 1 wherein R$^1$ represents a cyano group, R$^3$, R$^4$ and R$^5$ represent hydrogen atoms, G$^1$ represents a N atom and G$^2$ represents a —CR$^9$ group, wherein R$^9$ represents a phenyl group optionally substituted by one or more substituents selected from the group consisting of halogen atom, —COOH group and cyano group.

7. The compound according to claim 1 wherein R$^1$ represents a cyano group, R$^3$, R$^4$ and R$^5$ independently represent a hydrogen atom, G$^1$ represents a N atom and G$^2$ represents a —CR$^9$ group, wherein R$^9$ represents pyridyl ring optionally substituted by one or more substituents selected from the group consisting of halogen atom and cyano group.

8. The compound according to claim 1 wherein R$^1$ represents a cyano group, R$^3$, R$^4$ and R$^5$ independently represent a hydrogen atom, G$^2$ represents a N atom and G$^1$ represents a —CR$^9$ group, wherein R$^9$ is selected from:
  a) a phenyl group optionally substituted by one or more substituents selected from the group consisting of halogen atom, —COOH group and cyano group, and
  b) pyridyl ring optionally substituted by one or more substituents selected from the group consisting of halogen atom and cyano group.

9. The compound according to claim 2, wherein G$^1$ represents a N atom and G$^2$ represents a —CR$^9$ group, wherein R$^9$ is selected from the group consisting of:
  a) phenyl group optionally substituted by one or more substituents selected from the group consisting of halogen atom and —COOH group,
  b) a pyridyl ring optionally substituted by one or more substituents selected from the group consisting of halogen atom and cyano group, and
  c) a morpholinyl and piperazinyl group optionally substituted by a C$_1$-C$_3$ alkyl group or C$_3$-C$_6$ cycloalkyl group.

10. The compound according to claim 3, wherein $G^1$ represents a N atom and $G^2$ represents a —$CR^9$ group, wherein $R^9$ is selected from the group consisting of:
- a) phenyl group optionally substituted by one or more substituents selected from the group consisting of halogen atom and —COOH group,
- b) a pyridyl ring optionally substituted by one or more substituents selected from the group consisting of halogen atom and cyano group, and
- c) a morpholinyl and piperazinyl group optionally substituted by a $C_1$-$C_3$ alkyl group or $C_3$-$C_6$ cycloalkyl group.

11. The compound according to claim 2, wherein $G^2$ represents a N atom and $G^1$ represents a —$CR^9$ group, wherein $R^9$ is selected from the group consisting of:
- a) phenyl group optionally substituted by one or more substituents selected from the group consisting of halogen atom and —COOH group,
- b) pyridinyl ring optionally substituted by one or more substituents selected from the group consisting of halogen atom and cyano group, and
- c) a morpholinyl and piperazinyl groups optionally substituted by a group selected from of $C_1$-$C_3$ alkyl group and $C_3$-$C_6$ cycloalkyl group.

12. The compound according to claim 3, wherein $G^2$ represents a N atom and $G^1$ represents a —$CR^9$ group, wherein $R^9$ is selected from the group consisting of:
- a) phenyl group optionally substituted by one or more substituents selected from the group consisting of halogen atom and —COOH group,
- b) pyridinyl ring optionally substituted by one or more substituents selected from the group consisting of halogen atom and cyano group, and
- c) a morpholinyl and piperazinyl groups optionally substituted by a group selected from of $C_1$-$C_3$ alkyl group and $C_3$-$C_6$ cycloalkyl group.

13. The compound according to claim 1 which is:
2-chloro-5-cyano-N-(2-phenylpyridin-4-yl)benzamide
2-chloro-5-cyano-N-(6-phenylpyridin-3-yl)benzamide
2-chloro-5-cyano-N-(2-(4-fluorophenyl)pyridin-4-yl)benzamide
2-chloro-5-cyano-N-(6-(4-fluorophenyl)pyridin-3-yl)benzamide
N-([2,3'-bipyridin]-5-yl)-2-chloro-5-cyanobenzamide
N-([2,3'-bipyridin]-4-yl)-2-chloro-5-cyanobenzamide
N-([2,4'-bipyridin]-5-yl)-2-chloro-5-cyanobenzamide
N-([2,4'-bipyridin]-4-yl)-2-chloro-5-cyanobenzamide
N-([2,3'-bipyridin]-5-yl)-5-cyano-2-fluorobenzamide
5-cyano-2-fluoro-N-(6-(4-fluorophenyl)pyridin-3-yl)benzamide
5-cyano-2-fluoro-N-(2-(4-fluorophenyl)pyridin-4-yl)benzamide
N-([2,3'-bipyridin]-4-yl)-5-cyano-2-fluorobenzamide
N-([2,2'-bipyridin]-5-yl)-2-chloro-5-cyanobenzamide
2-chloro-5-cyano-N-(6-(4-methylpiperazin-1-yl)pyridin-3-yl)benzamide
2-chloro-5-cyano-N-(2-(4-methylpiperazin-1-yl)pyridin-4-yl)benzamide
2-chloro-5-cyano-N-(2-morpholinopyridin-4-yl)benzamide
2-chloro-5-cyano-N-(6-morpholinopyridin-3-yl)benzamide
N-([2,4'-bipyridin]-4-yl)-5-cyano-2-fluorobenzamide
N-([2,4'-bipyridin]-5-yl)-5-cyano-2-fluorobenzamide
2-chloro-5-cyano-N-(pyridazin-4-yl)benzamide
5-cyano-2-fluoro-N-(pyridazin-4-yl)benzamide
2-chloro-5-cyano-N-(6-cyclopropylpyridin-3-yl)benzamide
3-(5-(2-chloro-5-cyanobenzamido)pyridin-2-yl)benzoic acid
4-(5-(2-chloro-5-cyanobenzamido)pyridin-2-yl)benzoic acid, or
pharmaceutically acceptable salts thereof.

14. A pharmaceutical composition comprising a compound as defined in claim 1, a pharmaceutically acceptable diluent or carrier and optionally a therapeutically effective amount of further chemotherapeutics agents, anti-inflammatory agents, steroids, immunotherapeutic agent, or therapeutic antibodies.

15. A pharmaceutical composition according to claim 14 wherein the at least one therapeutic agent is selected from the group consisting of antibodies anti-CTLA4, antibodies anti-PD1, antibodies anti-PDL1; Carboplatin, Carmustine (BCNU), Cisplatin, Cyclophosphamide, Etoposide, Irinotecan, Lomustine (CCNU), Methotrexate, Procarbazine, Temozolomide or Vincristine.

16. A pharmaceutical composition according to claim 15 wherein the at least one therapeutic agent is selected from the group consisting of Ipilimumab, tremelimumab, MDX-1106 (nivolumab), MK3475 (pembrolizumab), CT-011 (pidilizumab), AMP-224, MPDL3280A, MEDI4736, MDX-1105; Carboplatin, Carmustine (BCNU), Cisplatin, Cyclophosphamide, Etoposide, Irinotecan, Lomustine (CCNU), Methotrexate, Procarbazine, Temozolomide or Vincristine.

17. A combination product comprising a compound as defined in claim 1 or a pharmaceutically acceptable salt thereof and at least a therapeutic agent selected from the group consisting of chemotherapeutics agents, anti-inflammatory agents, steroids, immunosuppressants, immunotherapeutic agents, therapeutic antibodies and PPAR modulators.

18. A method of treating diseases or pathological conditions that can be ameliorated by modulation of PPAR-gamma receptor comprising the administration to a patient in need thereof of a compound as defined in claim 1, wherein said disease or pathological condition is selected from the group consisting of cancer selected from breast cancer, pancreatic cancer, ovarian cancer, prostate cancer, renal cancer, bladder cancer, testicular cancer, urothelial cancer, skin cancer, melanoma, colon cancer, kidney cancer, brain cancer or a hematopoietic cancer selected from lymphoma, multiple myeloma and leukemia; metabolic diseases selected from osteoporosis, rachitis, arthrosis, obesity, type I and type II diabetes mellitus, lipid metabolism disorder, pancreatitis, glucose metabolism disorder, diabetic neuropathy, diabetic complications, hyperuricemia, inflammatory diseases selected from psoriasis, atopic dermatitis, eczema, acne vulgaris, other dermatitides and pruritu, pulmonary disorders selected from asthma, and chronic obstructive pulmonary disease, autoimmune disease, neurodegenerative disease selected from multiple sclerosis, Alzheimer's disease, Parkinson's disease, cardiovascular diseases selected from atherosclerosis, venous and arterial occlusive diseases, restenosis after invasive procedures, cardiomyopathy, myocardial fibrosis, congestive heart failure, angiogenesis and neovascularization in neoplastic diseases and renal diseases.

\* \* \* \* \*